United States Patent
De Keersmaecker et al.

(10) Patent No.: US 12,018,287 B2
(45) Date of Patent: Jun. 25, 2024

(54) RECOMBINANT PROTEIN PRODUCTION SYSTEM

(71) Applicant: Katholieke Universiteit Leuven, Leuven (BE)

(72) Inventors: Kim De Keersmaecker, Holsbeek (BE); Sergey O. Sulima, Leuven (BE); Tiziana Girardi, Boutersem (BE); Kim R Kampen, Leut (BE)

(73) Assignee: Katholieke Universiteit Leuven, Leuven (BE)

(*) Notice: Subject to any disclaimer, the term of this patent is extended or adjusted under 35 U.S.C. 154(b) by 1263 days.

(21) Appl. No.: 16/471,229

(22) PCT Filed: Dec. 22, 2017

(86) PCT No.: PCT/EP2017/084359
§ 371 (c)(1),
(2) Date: Jun. 19, 2019

(87) PCT Pub. No.: WO2018/115429
PCT Pub. Date: Jun. 28, 2018

(65) Prior Publication Data
US 2019/0360017 A1 Nov. 28, 2019

(30) Foreign Application Priority Data
Dec. 23, 2016 (GB) ...................................... 1622073

(51) Int. Cl.
| | |
|---|---|
| C12N 5/10 | (2006.01) |
| C12N 5/071 | (2010.01) |
| C12N 15/10 | (2006.01) |
| C12N 15/85 | (2006.01) |
| A01K 67/0278 | (2024.01) |
| C12P 21/02 | (2006.01) |
| G01N 33/68 | (2006.01) |

(52) U.S. Cl.
CPC ............ *C12N 5/10* (2013.01); *C12N 5/0602* (2013.01); *C12N 15/102* (2013.01); *C12N 15/85* (2013.01); *A01K 67/0278* (2013.01); *A01K 2217/072* (2013.01); *A01K 2227/105* (2013.01); *A01K 2267/01* (2013.01); *C12N 15/8509* (2013.01); *C12N 2015/8518* (2013.01); *C12N 2320/10* (2013.01); *C12N 2500/44* (2013.01); *C12P 21/02* (2013.01); *G01N 33/68* (2013.01); *G01N 2333/46* (2013.01)

(58) Field of Classification Search
CPC ...... C12N 5/10; C12N 5/0602; C12N 15/102; C12N 15/85; C12N 2320/10
USPC ............. 435/7.1, 7.21, 325, 69.1, 70.3, 455
See application file for complete search history.

(56) References Cited

U.S. PATENT DOCUMENTS

2008/0184384 A1* 7/2008 Dickman ........... C12N 15/8271
800/298

OTHER PUBLICATIONS

Hofer et al. (2007) J. Biol. Chem., vol. 282(45), 32630-32639.*
Keersmaecker et al. (2013) Nature Genetics, vol. 45(2), 186-191 and supplementary material.*
Cotter et al. (2000) J. Virol., vol. 74(3), 1486-1494.*
Klauck et al. (2006) Molecular Psychiatry., vol. 11, 1073-1084.*
Verbelen et al. (2022) Eng. Life Sci., vol. 22, 100-114.*
Advani et al., "Reprogramming the genetic code: the emerging role of ribosomal frameshifting in regulating cellular gene expression," Bioessays, Jan. 2016, 38(1): pp. 21-26.
Anzalone et al, "Reprogramming Eukaryotic Translation with Ligand-Responsive Synthetic RNA Switches," Nat Methods, May 2016, 13(5), pp. 453-458.
Belew et al, "PRFdb: A database of computationally predicted eurkaryotic programmed—I ribosomal frameshift signals," BMC Genomics, Jul. 2008, 9: 339.
Belew et al, "Ribosomal frameshifting in the CCR5 mRNA is regulated by miRNAs and the NMD pathway," Nature, Aug. 21, 2014, vol. 512, pp. 265-269.
Chen et al., "Tomato QM-Like Protein Protects *Saccharomyces cerevisiae* Cells against Oxidative Stress by Regulating Intracellular Proline Levels," Applied and Environmental Microbiology, Jun. 2006, vol. 72, No. 6, pp. 4001-4006.
Dahlmann et al., "Different Proteasome Subtypes in a Single Tissue Exhibit Different Enzymatic Properties," J. Mol. Biol., (2000), 303, pp. 643-653.
De Keersmaecker et al., "Exome sequencing identifies mutation in CNOT3 and ribosomal genes RPL5 and RPL10 in T-cell acute lymphoblastic leukemia," Nature Genetics, vol. 45, No. 2, Feb. 2013, pp. 186-190.
DeLabre, et al., "RPL29 codes for a non-essential protein of the 60S ribosomal subunit in *Saccharomyces cerevisiae* and exhibits synthetic lethality with mutations in genes for proteins required for subunit coupling," Biochimica et Biophysica Acta, 1574 (2002), pp. 255-261.
Girardi et al., "The T-cell leukemia associated ribosomal RPL10 R98S mutation enhances JAK-STAT signaling," Leukemia, Mar. 2018, 32(3), pp. 809-819.
Grentzmann et al, "A dual-luciferase reporter system for studying recoding signals," RNA (1998) 4, pp. 479-486.
Hara et al., "Two distinct functional high affinity receptors for mouse interleukin-3 (IL-3)," The EMBO Journal, vol. 11, No. 5, pp. 1875-1884, 1992.
Harger and Dinman, "An in vivo dual-luciferase assay system for studying translational recoding in the yeast *Saccharomyces cerevisiae*," RNA (2003), 9, pp. 1019-1024.

(Continued)

*Primary Examiner* — Anne Marie S Wehbe
(74) *Attorney, Agent, or Firm* — Dinsmore & Shohl LLP

(57) ABSTRACT

The present disclosure relates generally to an improved gene expression system in the field of recombinant gene expression. The invention relates to a system showing an improved yield and quality of protein production and methods for increasing production of a protein produced by cultured cells, particularly cultured eukaryotic cells.

11 Claims, 19 Drawing Sheets

Specification includes a Sequence Listing.

(56) References Cited

OTHER PUBLICATIONS

Hofer et al., "Mutational Analysis of the Ribosomal Protein Rpl10 from Yeast," Journal of Biological Chemistry, vol. 282, No. 45, pp. 32630-32639, Nov. 9, 2007.

Huber et al., "Immuno- and Constitutive Proteasome Crystal Structures Reveal Differences in Substrate and Inhibitor Specificity," Cell, 148, pp. 727-738, Feb. 17, 2012.

Jacobs and Dinman, "Systematic analysis of bicistronic reporter assay data," Nucleic Acids Research, 2004, vol. 32, No. 20, pp. 1-10.

Klare, et al., "Intermediate-type 20 S Proteasomes in HeLa Cells: "Asymmetric" Subunit Composition, Diversity and Adaptation," Journal of Molecular Biology, 2007, vol. 373, pp. 1-10.

Klauck et al., "Mutations in the ribosomal protein gene RPL10 suggest a novel modulating disease mechanism for autism," Molecular Psychiatry (2006), vol. 11, pp. 1073-1084.

Yu Lei, "Generation and Culture of Mouse Embryonic Fibroblasts," Mouse Models of Innate Immunity: Methods and Protocols, Methods in Molecular Biology, vol. 1031, pp. 59-64, (2013).

Li et al., "Transactivation of programmed ribosomal frameshifting by a viral protein," Proceedings of the National Academy of Sciences, May 13, 2014, E2172-E2181.

Mishto et al., "Proteasome isoforms exhibit only quantitative differences in cleavage and epitope generation," European Journal of Immunology, 2014, 44, pp. 3508-3621.

Mootha et al. "PGC-1α-responsive genes involved in oxidative phosphorylation are coordinately downregulated in human diabetes," Nature Genetics, vol. 34, No. 3, Jul. 2003, pp. 267-273.

Reimand et al., "g:Profiler—a web server for functional interpretation of gene lists (2016 update)," Nucleic Acids Research, 2016, vol. 44, Web Server Issue W83-W89.

Ribeiro et al., "IL-7R-mediated signalling in T-cell acute lymphoblastic leukemia," Advances in Biological Regulation, 53, 2013, pp. 211-222.

Subramanian, et al., "Gene set enrichment analysis: A knowledge-based approach for interpreting genome-wide expression profiles," Proceedings of the National Academy of Sciences; Oct. 25, 2005, vol. 102, No. 43, pp. 15545-15550.

Sulima, et al., "Bypass of the pre-60S ribosomal quality control as a pathway to oncogenesis," Proceedings of the National Academy of Sciences, Apr. 15, 2014, vol. 111, No. 15, pp. 5640-5645.

Van Vlierberghe, et al., "The molecular basis of T cell acute lymphoblastic leukemia," The Journal of Clinical Investigation; vol. 122, No. 10, Oct. 2012, pp. 3398-3406.

Van der Krogt, et al., "Anaplastic lymphoma kinase-positive analplastic large cell lymphoma with the variant RNF213- ATIC- and TPM3-ALK fusions is characterized by number gain of the rearranged ALK gene," Haematologica, vol. 102, 2017, pp. 1605-1616.

International Search Report and Written Opinion dated May 7, 2018 in related International Application No. PCT/EP2017/084359.

Written Opinion of International Searching Authority dated May 7, 2018 in related International Application No. PCT/EP2017/084359.

\* cited by examiner

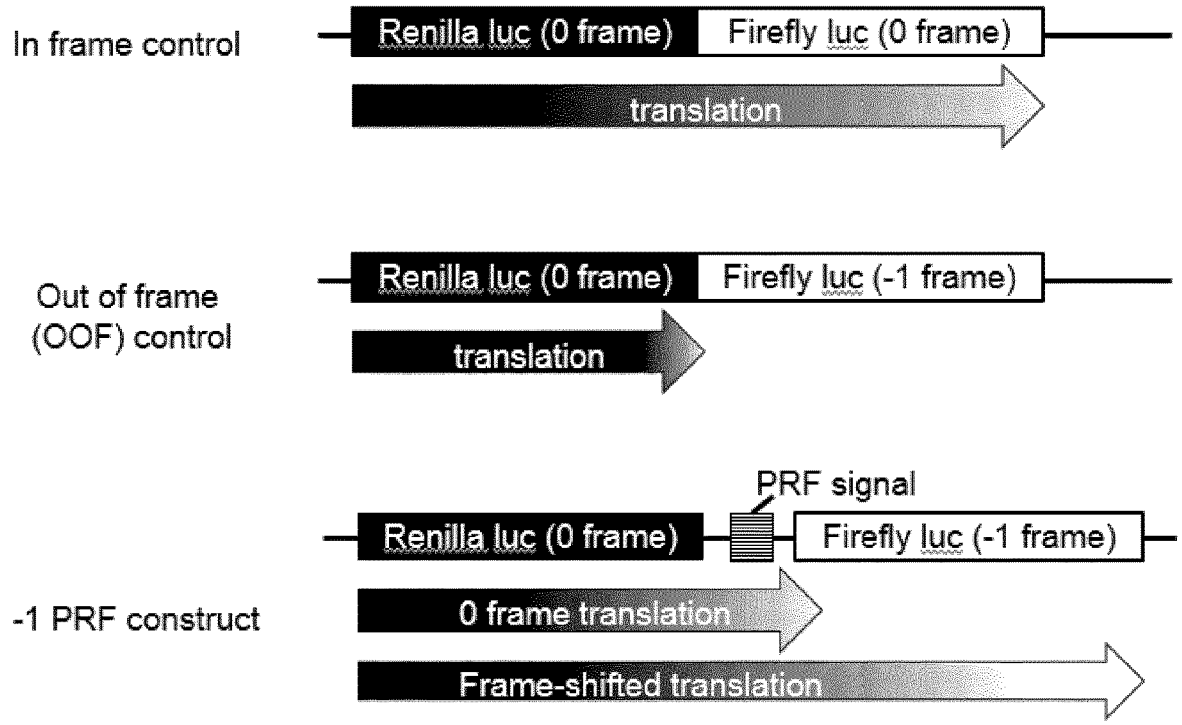
Figure 1
Stop codon read-through reporter assay:
Missense suppression reporter assay:
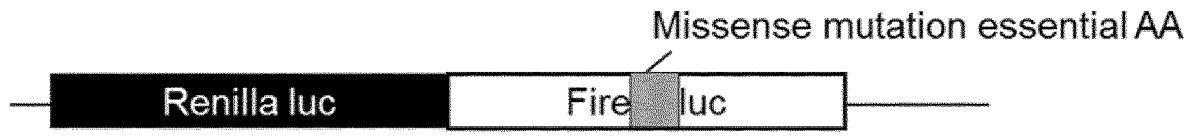
Figure 2

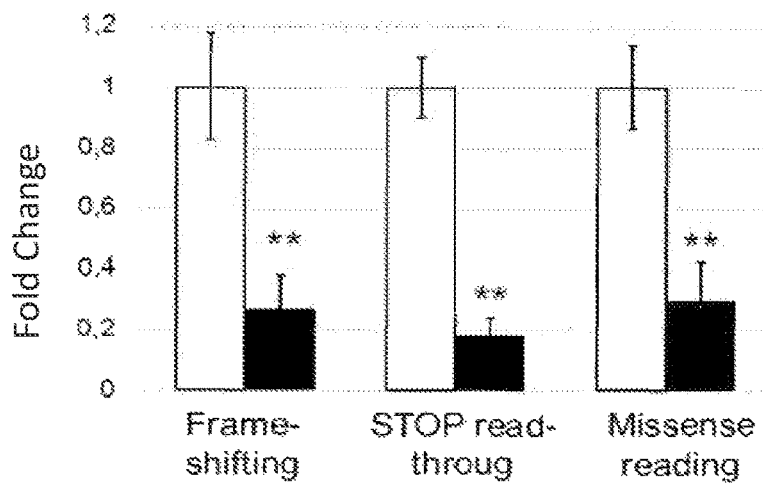
Figure 4
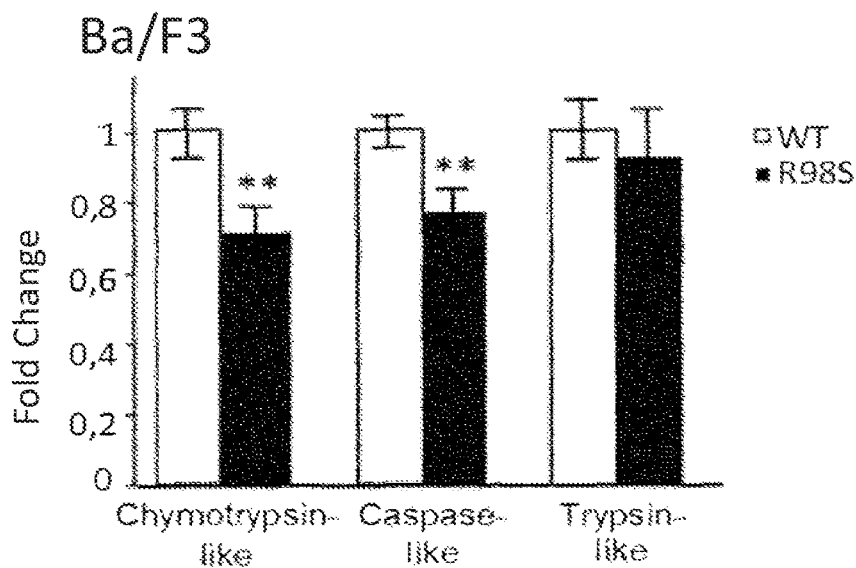
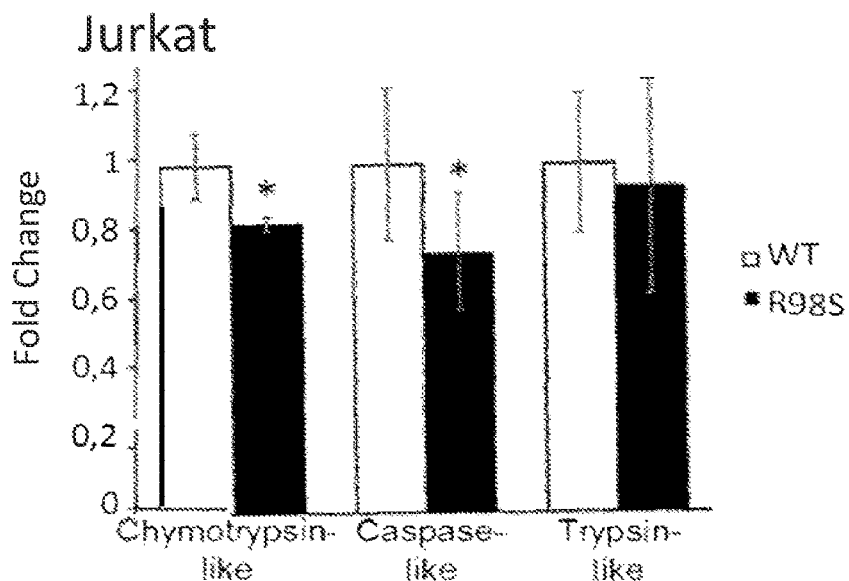
Figure 5

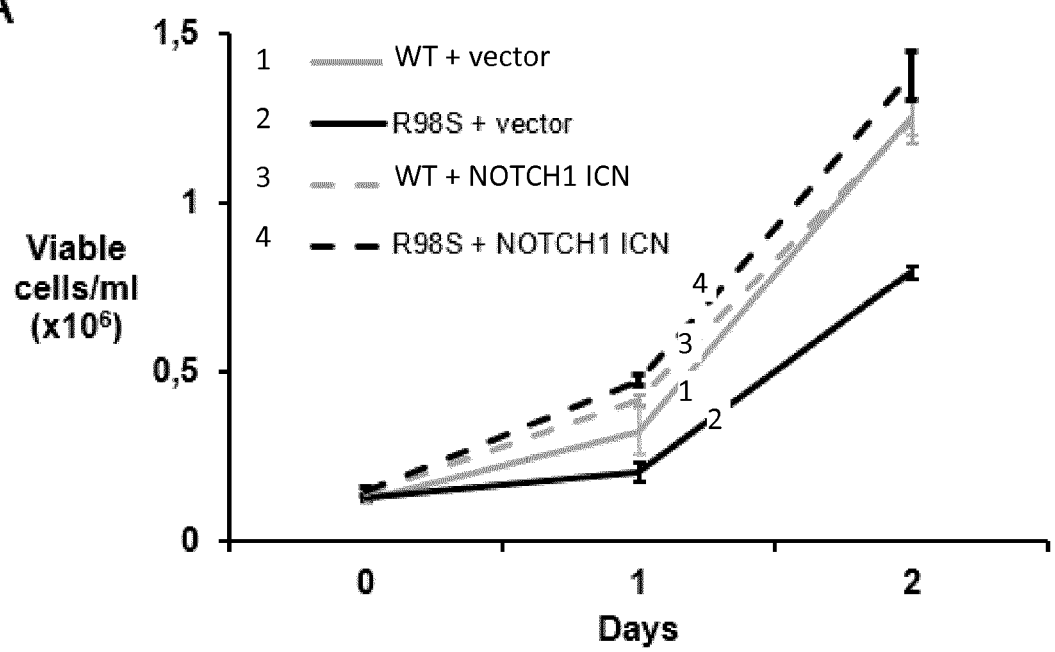
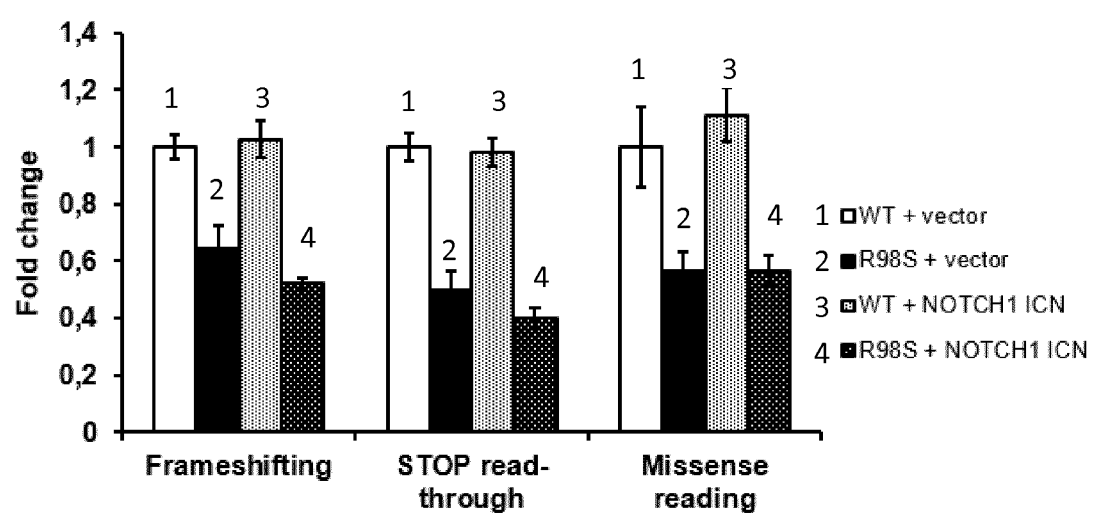
Figure 6

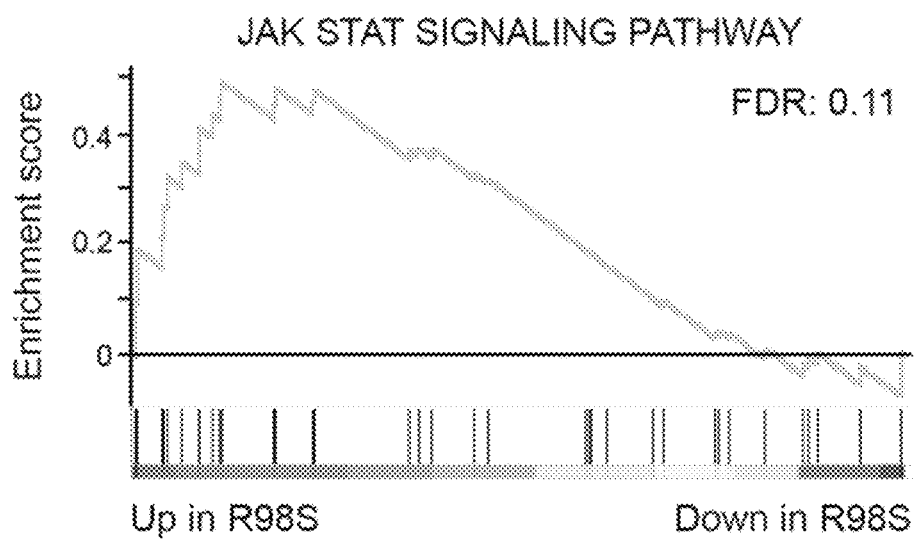
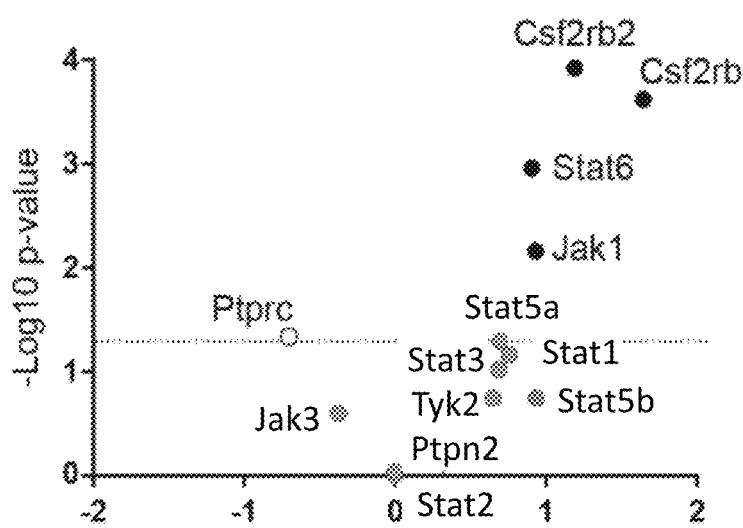
Figure 10

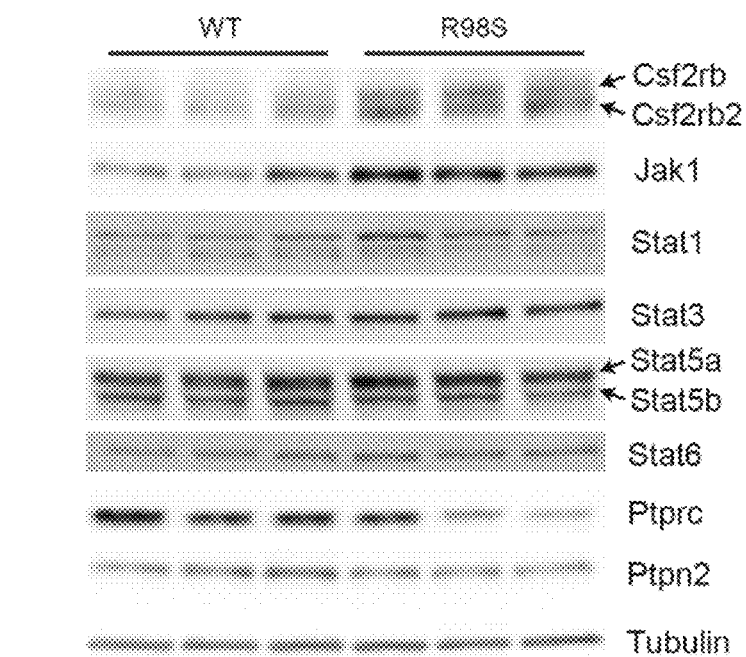
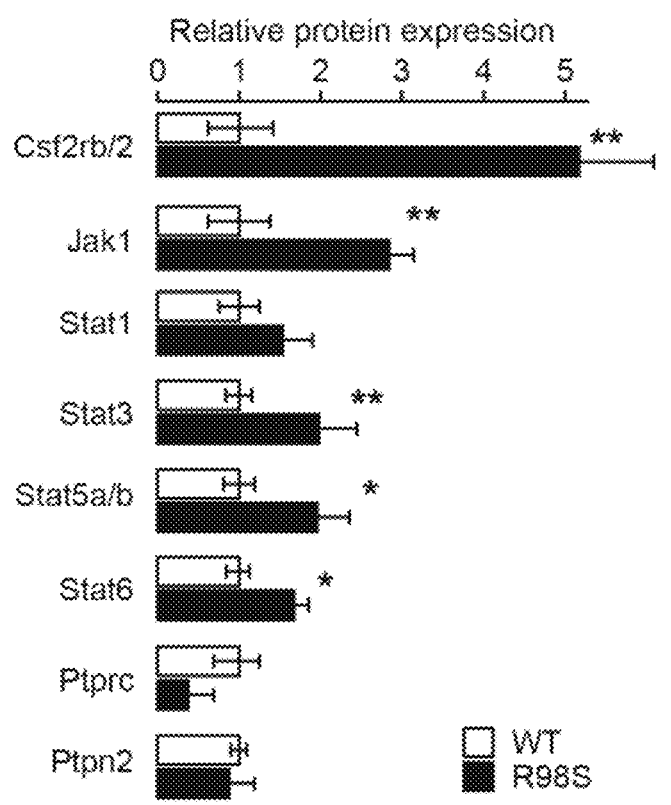
Figure 10 (continued)

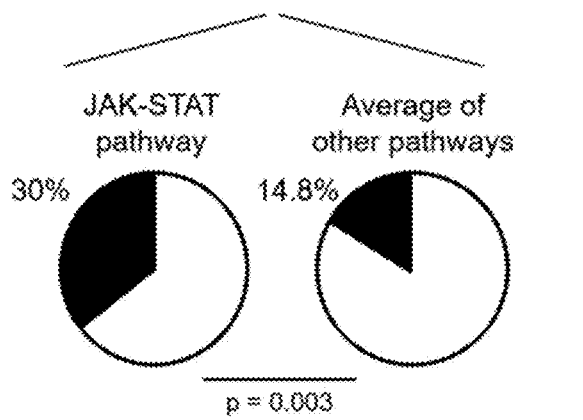
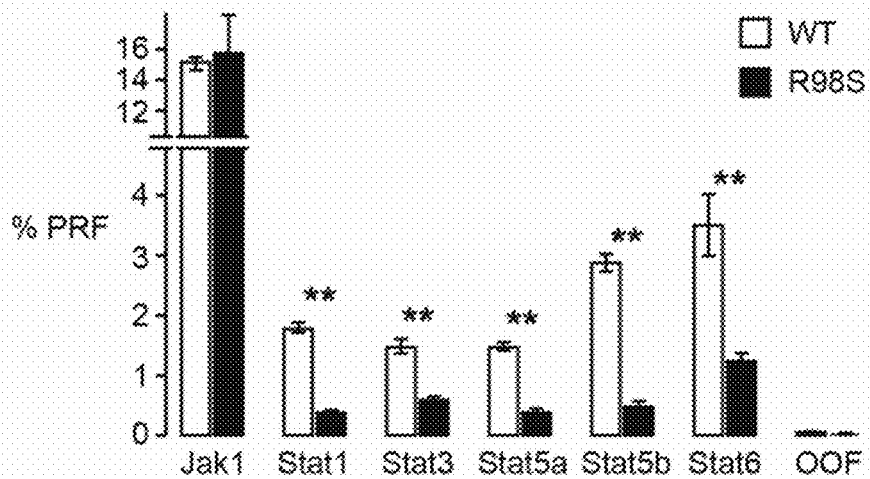
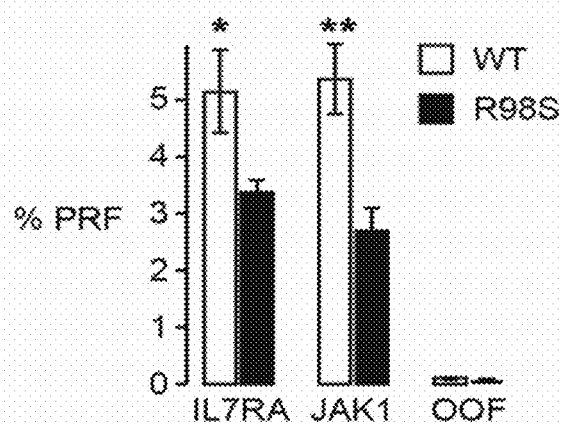
Figure 12

E
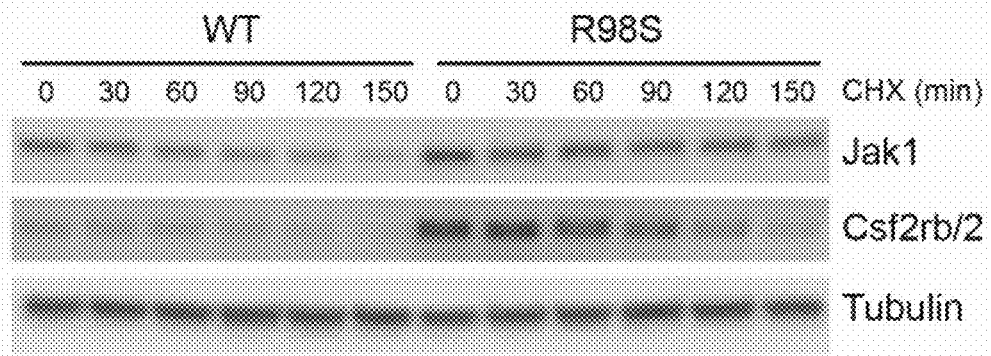
F
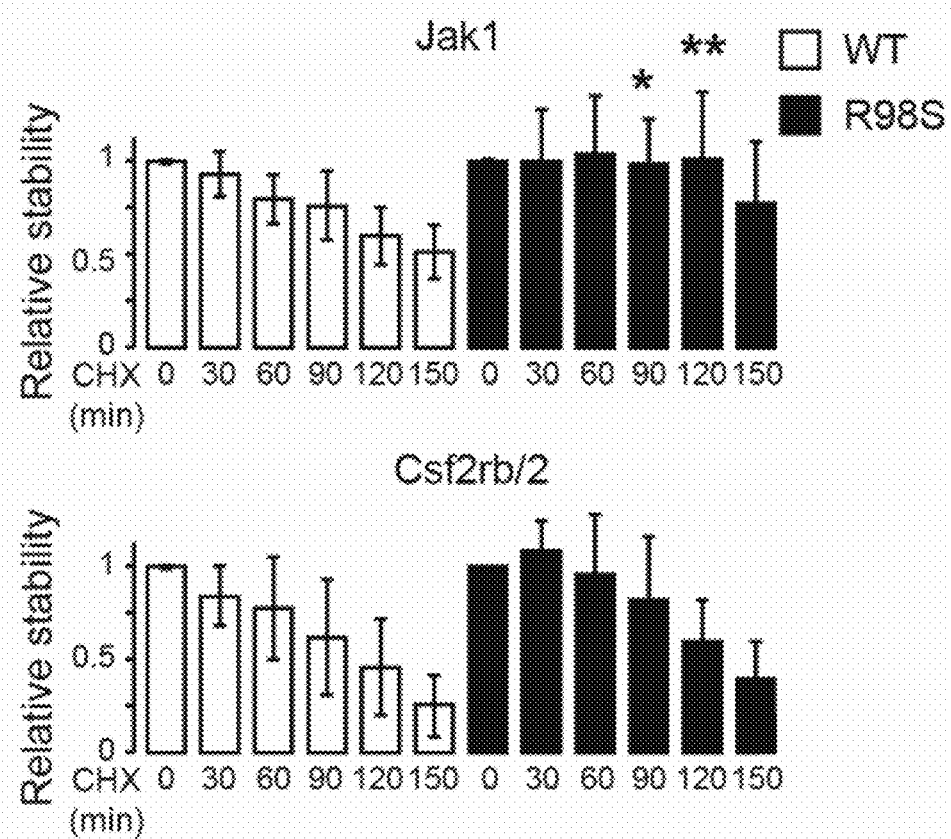
Figure 13 (continued)

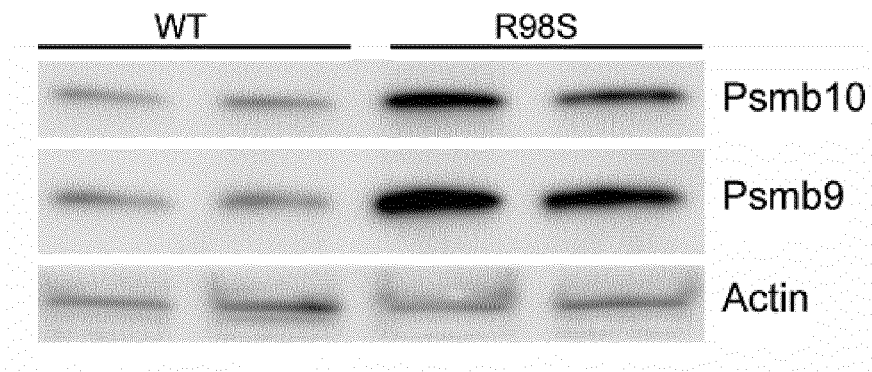
Figure 16
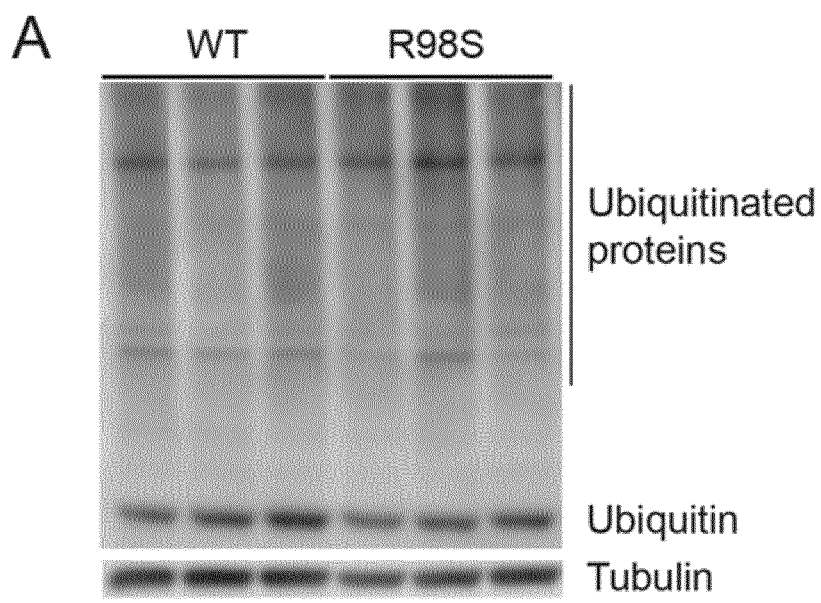
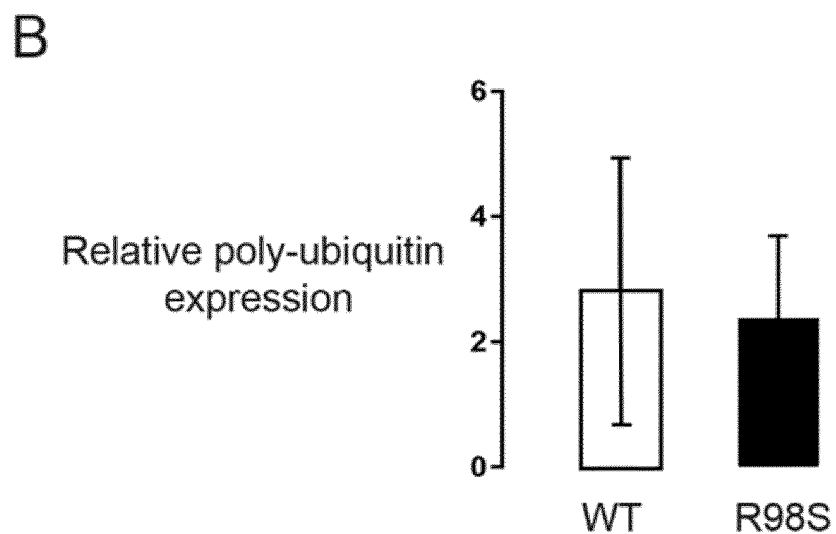
Figure 17

```
                          1         2         3         4         5
                 12345678901234567890123456789012345678901234567890
Human            MGRRPARCYRYCKNKPYPKSRFCRGVPDAKIRIFDLGRKKAKVDEFPLCG
Mouse            MGRRPARCYRYCKNKPYPKSRFCRGVPDAKIRIFDLGRKKAKVDEFPLCG
Yeast            MARRPARCYRYQKNKPYPKSRYNRAVPDSKIRIYDLGKKKATVDEFPLCV
                                                 *
                                                 33

6         7         8         9        10
                 12345678901234567890123456789012345678901234567890
Human            HMVSDEYEQLSSEALEAARICANKYMVKSCGKDGFHIRVRLHPFHVIRIN
Mouse            HMVSDEYEQLSSEALEAARICANKYMVKSCGKDGFHIRVRLHPFHVIRIN
Yeast            HLVSNELEQLSSEALEAARICANKYMTTVSGRDAFHLRVRVHPFHVLRIN
                   *       *                                    *
                  66      10                                    98

11        12        13        14        15
                 12345678901234567890123456789012345678901234567890
Human            KMLSCAGADRLQTGMRGAFGKPQGTVARVHIGQVIMSIRTKLQNKEHVIE
Mouse            KMLSCAGADRLQTGMRGAFGKPQGTVARVHIGQVIMSIRTKLQNKEHVIE
Yeast            KMLSCAGADRLQQGMRGAWGKPHGLAARVDIGQIIFSVRTKDSNKDVVVE
                                     *
                                    123

16        17        18        19        20
                 12345678901234567890123456789012345678901234567890
Human            ALRRAKFKFPGRQKIHISKKWGFTKFNADEFEDMVAEKRLIPDGCGVKYI
Mouse            ALRRAKFKFPGRQKIHISKKWGFTKFNADEFEDMVAEKRLIPDGCGVKYI
Yeast            GLRRARYKFPGQQKIILSKKWGFTNLDRPEYLKKREAGEVKDDGAFVKFL 21        22
                 123456789012345678901
Human            PSRGPLDKWALHS--------            [SEQ ID NO:2]
Mouse            PNRGPLDKWALHS--------            [SEQ ID NO:3]
Yeast            SKKGSLENNIREFPEYFAAQA            [SEQ ID NO:4]
```

Figure 19

SEQUENCE LISTING

<160> NUMBER OF SEQ ID NOS: 12

<210> SEQ ID NO 1
<211> LENGTH: 645
<212> TYPE: DNA
<213> ORGANISM: Homo sapiens
<220> FEATURE:
<221> NAME/KEY: misc_feature
<222> LOCATION: (1)..(645)
<223> OTHER INFORMATION: Human RPL10 cDNA sequence
<220> FEATURE:
<221> NAME/KEY: CDS
<222> LOCATION: (1)..(645)

<400> SEQUENCE: 1

```
atg ggc cgc cgc ccc gcc cgt tgt tac cgg tat tgt aag aac aag ccg      48
Met Gly Arg Arg Pro Ala Arg Cys Tyr Arg Tyr Cys Lys Asn Lys Pro
 1               5                  10                  15 tac cca aag tct cgc ttc tgc cga ggt gtc cct gat gcc aag att cgc      96
Tyr Pro Lys Ser Arg Phe Cys Arg Gly Val Pro Asp Ala Lys Ile Arg
            20                  25                  30 att ttt gac ctg ggg cgg aaa aag gca aaa gtg gat gag ttt ccg ctt     144
Ile Phe Asp Leu Gly Arg Lys Lys Ala Lys Val Asp Glu Phe Pro Leu
        35                  40                  45 tgt ggc cac atg gtg tca gat gaa tat gag cag ctg tcc tct gaa gcc     192
Cys Gly His Met Val Ser Asp Glu Tyr Glu Gln Leu Ser Ser Glu Ala
    50                  55                  60
```

```
ctg gag gct gcc cga att tgt gcc aat aag tac atg gta aaa agt tgt        240
Leu Glu Ala Ala Arg Ile Cys Ala Asn Lys Tyr Met Val Lys Ser Cys
 65                  70                  75                  80 ggc aaa gat ggc ttc cat atc cgg gtg cgg ctc cac ccc ttc cac gtc        288
Gly Lys Asp Gly Phe His Ile Arg Val Arg Leu His Pro Phe His Val
                 85                  90                  95 atc cgc atc aac aag atg ttg tcc tgt gct ggg gct gac agg ctc caa        336
Ile Arg Ile Asn Lys Met Leu Ser Cys Ala Gly Ala Asp Arg Leu Gln
            100                 105                 110 aca ggc atg cga ggt gcc ttt gga aag ccc cag ggc act gtg gcc agg        384
Thr Gly Met Arg Gly Ala Phe Gly Lys Pro Gln Gly Thr Val Ala Arg
        115                 120                 125 gtt cac att ggc caa gtt atc atg tcc atc cgc acc aag ctg cag aac        432
Val His Ile Gly Gln Val Ile Met Ser Ile Arg Thr Lys Leu Gln Asn
130                 135                 140 aag gag cat gtg att gag gcc ctg cgc agg gcc aag ttc aag ttt cct        480
Lys Glu His Val Ile Glu Ala Leu Arg Arg Ala Lys Phe Lys Phe Pro
145                 150                 155                 160 ggc cgc cag aag atc cac atc tca aag aag tgg ggc ttc acc aag ttc        528
Gly Arg Gln Lys Ile His Ile Ser Lys Lys Trp Gly Phe Thr Lys Phe
                165                 170                 175 aat gct gat gaa ttt gaa gac atg gtg gct gaa aag cgg ctc atc cca        576
Asn Ala Asp Glu Phe Glu Asp Met Val Ala Glu Lys Arg Leu Ile Pro
            180                 185                 190 gat ggc tgt ggg gtc aag tac atc ccc agt cgt ggc cct ctg gac aag        624
Asp Gly Cys Gly Val Lys Tyr Ile Pro Ser Arg Gly Pro Leu Asp Lys
        195                 200                 205 tgg cgg gcc ctg cac tca tga                                            645
Trp Arg Ala Leu His Ser
    210
```

<210> SEQ ID NO 2
<211> LENGTH: 214
<212> TYPE: PRT
<213> ORGANISM: Homo sapiens

<400> SEQUENCE: 2

```
Met Gly Arg Arg Pro Ala Arg Cys Tyr Arg Tyr Cys Lys Asn Lys Pro
 1               5                  10                  15

Tyr Pro Lys Ser Arg Phe Cys Arg Gly Val Pro Asp Ala Lys Ile Arg
            20                  25                  30

Ile Phe Asp Leu Gly Arg Lys Lys Ala Lys Val Asp Glu Phe Pro Leu
        35                  40                  45

Cys Gly His Met Val Ser Asp Glu Tyr Glu Gln Leu Ser Ser Glu Ala
    50                  55                  60

Leu Glu Ala Ala Arg Ile Cys Ala Asn Lys Tyr Met Val Lys Ser Cys
 65                  70                  75                  80

Gly Lys Asp Gly Phe His Ile Arg Val Arg Leu His Pro Phe His Val
                 85                  90                  95

Ile Arg Ile Asn Lys Met Leu Ser Cys Ala Gly Ala Asp Arg Leu Gln
            100                 105                 110

Thr Gly Met Arg Gly Ala Phe Gly Lys Pro Gln Gly Thr Val Ala Arg
        115                 120                 125

Val His Ile Gly Gln Val Ile Met Ser Ile Arg Thr Lys Leu Gln Asn
130                 135                 140

Lys Glu His Val Ile Glu Ala Leu Arg Arg Ala Lys Phe Lys Phe Pro
145                 150                 155                 160
```

```
Gly Arg Gln Lys Ile His Ile Ser Lys Lys Trp Gly Phe Thr Lys Phe
                165                 170                 175

Asn Ala Asp Glu Phe Glu Asp Met Val Ala Glu Lys Arg Leu Ile Pro
            180                 185                 190

Asp Gly Cys Gly Val Lys Tyr Ile Pro Ser Arg Gly Pro Leu Asp Lys
        195                 200                 205

Trp Arg Ala Leu His Ser
    210

<210> SEQ ID NO 3
<211> LENGTH: 213
<212> TYPE: PRT
<213> ORGANISM: Mus musculus
<220> FEATURE:
<221> NAME/KEY: MISC_FEATURE
<222> LOCATION: (1)..(213)
<223> OTHER INFORMATION: mouse RPL10 protein sequence

<400> SEQUENCE: 3

Met Gly Arg Arg Pro Ala Arg Cys Tyr Arg Tyr Cys Lys Asn Lys Pro
1               5                   10                  15

Tyr Pro Lys Ser Arg Phe Cys Arg Gly Val Pro Asp Ala Lys Ile Arg
            20                  25                  30

Ile Phe Asp Leu Gly Arg Lys Lys Ala Lys Val Asp Glu Phe Pro Leu
        35                  40                  45

Cys Gly His Met Val Ser Asp Glu Tyr Glu Gln Leu Ser Ser Glu Ala
    50                  55                  60

Leu Glu Ala Ala Arg Ile Cys Ala Asn Lys Tyr Met Val Lys Ser Cys
65                  70                  75                  80

Gly Lys Asp Gly Phe His Ile Arg Val Arg Leu His Pro Phe His Val
                85                  90                  95

Ile Arg Ile Asn Lys Met Leu Ser Cys Ala Gly Ala Asp Arg Leu Gln
            100                 105                 110

Thr Gly Met Arg Gly Ala Phe Gly Lys Pro Gln Gly Thr Val Ala Arg
        115                 120                 125

Val His Ile Gly Gln Val Ile Met Ser Ile Arg Thr Lys Leu Gln Asn
    130                 135                 140

Lys Glu His Val Ile Glu Ala Leu Arg Arg Ala Lys Phe Lys Phe Pro
145                 150                 155                 160

Gly Arg Gln Lys Ile His Ile Ser Lys Lys Trp Gly Phe Thr Lys Phe
                165                 170                 175

Asn Ala Asp Glu Phe Glu Asp Met Val Ala Glu Lys Arg Leu Ile Pro
            180                 185                 190

Asp Gly Cys Gly Val Lys Tyr Ile Pro Asn Arg Gly Pro Leu Asp Lys
        195                 200                 205

Trp Ala Leu His Ser
    210

<210> SEQ ID NO 4
<211> LENGTH: 221
<212> TYPE: PRT
<213> ORGANISM: Saccharomyces cerevisiae
<220> FEATURE:
<221> NAME/KEY: MISC_FEATURE
<222> LOCATION: (1)..(221)
<223> OTHER INFORMATION: yeast RPL10 protein sequence

<400> SEQUENCE: 4

Met Ala Arg Arg Pro Ala Arg Cys Tyr Arg Tyr Gln Lys Asn Lys Pro
```

```
                1               5                   10                  15
                Tyr Pro Lys Ser Arg Tyr Asn Arg Ala Val Pro Asp Ser Lys Ile Arg
                            20                  25                  30

Ile Tyr Asp Leu Gly Lys Lys Lys Ala Thr Val Asp Glu Phe Pro Leu
                            35                  40                  45

Cys Val His Leu Val Ser Asn Glu Leu Glu Gln Leu Ser Ser Glu Ala
                            50                  55                  60

Leu Glu Ala Ala Arg Ile Cys Ala Asn Lys Tyr Met Thr Thr Val Ser
                65                          70                  75                  80

Gly Arg Asp Ala Phe His Leu Arg Val Arg Val His Pro Phe His Val
                                        85                  90                  95

Leu Arg Ile Asn Lys Met Leu Ser Cys Ala Gly Ala Asp Arg Leu Gln
                                100                 105                 110

Gln Gly Met Arg Gly Ala Trp Gly Lys Pro His Gly Leu Ala Ala Arg
                            115                 120                 125

Val Asp Ile Gly Gln Ile Ile Phe Ser Val Arg Thr Lys Asp Ser Asn
                    130                 135                 140

Lys Asp Val Val Val Glu Gly Leu Arg Arg Ala Arg Tyr Lys Phe Pro
                145                 150                 155                 160

Gly Gln Gln Lys Ile Ile Leu Ser Lys Lys Trp Gly Phe Thr Asn Leu
                                165                 170                 175

Asp Arg Pro Glu Tyr Leu Lys Lys Arg Glu Ala Gly Glu Val Lys Asp
                            180                 185                 190

Asp Gly Ala Phe Val Lys Phe Leu Ser Lys Lys Gly Ser Leu Glu Asn
                            195                 200                 205

Asn Ile Arg Glu Phe Pro Glu Tyr Phe Ala Ala Gln Ala
                            210                 215                 220

<210> SEQ ID NO 5
<211> LENGTH: 2772
<212> TYPE: DNA
<213> ORGANISM: Artificial Sequence
<220> FEATURE:
<223> OTHER INFORMATION: construct comprising human intracellular NOTCH
<220> FEATURE:
<221> NAME/KEY: misc_feature
<222> LOCATION: (1)..(2772)
<223> OTHER INFORMATION: human Notch
<220> FEATURE:
<221> NAME/KEY: CDS
<222> LOCATION: (1)..(2772)

<400> SEQUENCE: 5 atg ccg ccg ctc ctg gcg ccc ctg ctc tgc ctg gcg ctg ctg ccc gcg      48
Met Pro Pro Leu Leu Ala Pro Leu Leu Cys Leu Ala Leu Leu Pro Ala
1               5                   10                  15 ctc gcc gca cga ggc ccg cga gga tcc atc gtc tac ctg gag att gac      96
Leu Ala Ala Arg Gly Pro Arg Gly Ser Ile Val Tyr Leu Glu Ile Asp
                20                  25                  30 aac cgg cag tgt gtg cag gcc tcc tcg cag tgc ttc cag agt gcc acc     144
Asn Arg Gln Cys Val Gln Ala Ser Ser Gln Cys Phe Gln Ser Ala Thr
            35                  40                  45 gac gtg gcc gca ttc ctg gga gcg ctc gcc tcg ctg ggc agc ctc aac     192
Asp Val Ala Ala Phe Leu Gly Ala Leu Ala Ser Leu Gly Ser Leu Asn
        50                  55                  60 atc ccc tac aag atc gag gcc gtg cag agt gag acc gtg gag ccg ccc     240
Ile Pro Tyr Lys Ile Glu Ala Val Gln Ser Glu Thr Val Glu Pro Pro
65                  70                  75                  80 ccg ccg gcg cag ctg cac ttc atg tac gtg gcg cag gcc gtg gag ccg     288
```

```
            Pro Pro Ala Gln Leu His Phe Met Tyr Val Ala Gln Ala Val Glu Pro
                            85              90              95 ccc ccg ccg gcg cag ctg cac ttc atg tac gtg gcg gcg gcc ttt              336
Pro Pro Pro Ala Gln Leu His Phe Met Tyr Val Ala Ala Ala Phe
                100             105             110 gtg ctt ctg ttc ttc gtg ggc tgc ggg gtg ctg ctg tcc cgc aag cgc          384
Val Leu Leu Phe Phe Val Gly Cys Gly Val Leu Leu Ser Arg Lys Arg
            115             120             125 cgg cgg cag cat ggc cag ctc tgg ttc cct gag ggc ttc aaa gtg tct          432
Arg Arg Gln His Gly Gln Leu Trp Phe Pro Glu Gly Phe Lys Val Ser
    130             135             140 gag gcc agc aag aag aag cgg cgg gag ccc ctc ggc gag gac tcc gtg          480
Glu Ala Ser Lys Lys Lys Arg Arg Glu Pro Leu Gly Glu Asp Ser Val
145             150             155             160 ggc ctc aag ccc ctg aag aac gct tca gac ggt gcc ctc atg gac gac          528
Gly Leu Lys Pro Leu Lys Asn Ala Ser Asp Gly Ala Leu Met Asp Asp
                165             170             175 aac cag aat gag tgg ggg gac gag gac ctg gag acc aag aag ttc cgg          576
Asn Gln Asn Glu Trp Gly Asp Glu Asp Leu Glu Thr Lys Lys Phe Arg
            180             185             190 ttc gag gag ccc gtg gtt ctg cct gac ctg gac gac cag aca gac cac          624
Phe Glu Glu Pro Val Val Leu Pro Asp Leu Asp Asp Gln Thr Asp His
    195             200             205 cgg cag tgg act cag cag cac ctg gat gcc gct gac ctg cgc atg tct          672
Arg Gln Trp Thr Gln Gln His Leu Asp Ala Ala Asp Leu Arg Met Ser
210             215             220 gcc atg gcc ccc aca ccg ccc cag ggt gag gtt gac gcc gac tgc atg          720
Ala Met Ala Pro Thr Pro Pro Gln Gly Glu Val Asp Ala Asp Cys Met
225             230             235             240 gac gtc aat gtc cgc ggg cct gat ggc ttc acc ccg ctc atg atc gcc          768
Asp Val Asn Val Arg Gly Pro Asp Gly Phe Thr Pro Leu Met Ile Ala
                245             250             255 tcc tgc agc ggg ggc ggc ctg gag acg ggc aac agc gag gaa gag gag          816
Ser Cys Ser Gly Gly Gly Leu Glu Thr Gly Asn Ser Glu Glu Glu Glu
            260             265             270 gac gcg ccg gcc gtc atc tcc gac ttc atc tac cag ggc gcc agc ctg          864
Asp Ala Pro Ala Val Ile Ser Asp Phe Ile Tyr Gln Gly Ala Ser Leu
    275             280             285 cac aac cag aca gac cgc acg ggc gag acc gcc ttg cac ctg gcc gcc          912
His Asn Gln Thr Asp Arg Thr Gly Glu Thr Ala Leu His Leu Ala Ala
290             295             300 cgc tac tca cgc tct gat gcc gcc aag cgc ctg ctg gag gcc agc gca          960
Arg Tyr Ser Arg Ser Asp Ala Ala Lys Arg Leu Leu Glu Ala Ser Ala
305             310             315             320 gat gcc aac atc cag gac aac atg ggc cgc acc ccg ctg cat gcg gct         1008
Asp Ala Asn Ile Gln Asp Asn Met Gly Arg Thr Pro Leu His Ala Ala
                325             330             335 gtg tct gcc gac gca caa ggt gtc ttc cag atc ctg atc cgg aac cga         1056
Val Ser Ala Asp Ala Gln Gly Val Phe Gln Ile Leu Ile Arg Asn Arg
            340             345             350 gcc aca gac ctg gat gcc cgc atg cat gat ggc acg acg cca ctg atc         1104
Ala Thr Asp Leu Asp Ala Arg Met His Asp Gly Thr Thr Pro Leu Ile
    355             360             365 ctg gct gcc cgc ctg gcc gtg gag ggc atg ctg gag gac ctc atc aac         1152
Leu Ala Ala Arg Leu Ala Val Glu Gly Met Leu Glu Asp Leu Ile Asn
370             375             380 tca cac gcc gac gtc aac gcc gta gat gac ctg ggc aag tcc gcc ctg         1200
Ser His Ala Asp Val Asn Ala Val Asp Asp Leu Gly Lys Ser Ala Leu
385             390             395             400
```

|  |  |
|---|---|
| cac tgg gcc gcc gcc gtg aac aat gtg gat gcc gca gtt gtg ctc ctg<br>His Trp Ala Ala Ala Val Asn Asn Val Asp Ala Ala Val Val Leu Leu<br>                            405                          410                          415 | 1248 |
| aag aac ggg gct aac aaa gat atg cag aac aac agg gag gag aca ccc<br>Lys Asn Gly Ala Asn Lys Asp Met Gln Asn Asn Arg Glu Glu Thr Pro<br>                    420                          425                          430 | 1296 |
| ctg ttt ctg gcc gcc cgg gag ggc agc tac gag acc gcc aag gtg ctg<br>Leu Phe Leu Ala Ala Arg Glu Gly Ser Tyr Glu Thr Ala Lys Val Leu<br>                            435                          440                          445 | 1344 |
| ctg gac cac ttt gcc aac cgg gac atc acg gat cat atg gac cgc ctg<br>Leu Asp His Phe Ala Asn Arg Asp Ile Thr Asp His Met Asp Arg Leu<br>                450                          455                          460 | 1392 |
| ccg cgc gac atc gca cag gag cgc atg cat cac gac atc gtg agg ctg<br>Pro Arg Asp Ile Ala Gln Glu Arg Met His His Asp Ile Val Arg Leu<br>465                          470                          475                          480 | 1440 |
| ctg gac gag tac aac ctg gtg cgc agc ccg cag ctg cac gga gcc ccg<br>Leu Asp Glu Tyr Asn Leu Val Arg Ser Pro Gln Leu His Gly Ala Pro<br>                                485                          490                          495 | 1488 |
| ctg ggg ggc acg ccc acc ctg tcg ccc ccg ctc tgc tcg ccc aac ggc<br>Leu Gly Gly Thr Pro Thr Leu Ser Pro Pro Leu Cys Ser Pro Asn Gly<br>              500                          505                          510 | 1536 |
| tac ctg ggc agc ctc aag ccc ggc gtg cag ggc aag aag gtc cgc aag<br>Tyr Leu Gly Ser Leu Lys Pro Gly Val Gln Gly Lys Lys Val Arg Lys<br>                            515                          520                          525 | 1584 |
| ccc agc agc aaa ggc ctg gcc tgt gga agc aag gag gcc aag gac ctc<br>Pro Ser Ser Lys Gly Leu Ala Cys Gly Ser Lys Glu Ala Lys Asp Leu<br>          530                          535                          540 | 1632 |
| aag gca cgg agg aag aag tcc cag gac ggc aag ggc tgc ctg ctg gac<br>Lys Ala Arg Arg Lys Lys Ser Gln Asp Gly Lys Gly Cys Leu Leu Asp<br>545                          550                          555                          560 | 1680 |
| agc tcc ggc atg ctc tcg ccc gtg gac tcc ctg gag tca ccc cat ggc<br>Ser Ser Gly Met Leu Ser Pro Val Asp Ser Leu Glu Ser Pro His Gly<br>                                565                          570                          575 | 1728 |
| tac ctg tca gac gtg gcc tcg ccg cca ctg ctg ccc tcc ccg ttc cag<br>Tyr Leu Ser Asp Val Ala Ser Pro Pro Leu Leu Pro Ser Pro Phe Gln<br>              580                          585                          590 | 1776 |
| cag tct ccg tcc gtg ccc ctc aac cac ctg cct ggg atg ccc gac acc<br>Gln Ser Pro Ser Val Pro Leu Asn His Leu Pro Gly Met Pro Asp Thr<br>          595                          600                          605 | 1824 |
| cac ctg ggc atc ggg cac ctg aac gtg gcg gcc aag ccc gag atg gcg<br>His Leu Gly Ile Gly His Leu Asn Val Ala Ala Lys Pro Glu Met Ala<br>                    610                          615                          620 | 1872 |
| gcg ctg ggt ggg ggc ggc cgg ctg gcc ttt gag act ggc cca cct cgt<br>Ala Leu Gly Gly Gly Gly Arg Leu Ala Phe Glu Thr Gly Pro Pro Arg<br>625                          630                          635                          640 | 1920 |
| ctc tcc cac ctg cct gtg gcc tct ggc acc agc acc gtc ctg ggc tcc<br>Leu Ser His Leu Pro Val Ala Ser Gly Thr Ser Thr Val Leu Gly Ser<br>                            645                          650                          655 | 1968 |
| agc agc gga ggg gcc ctg aat ttc act gtg ggc ggg tcc acc agt ttg<br>Ser Ser Gly Gly Ala Leu Asn Phe Thr Val Gly Gly Ser Thr Ser Leu<br>                    660                          665                          670 | 2016 |
| aat ggt caa tgc gag tgg ctg tcc cgg ctg cag agc ggc atg gtg ccg<br>Asn Gly Gln Cys Glu Trp Leu Ser Arg Leu Gln Ser Gly Met Val Pro<br>              675                          680                          685 | 2064 |
| aac caa tac aac cct ctg cgg ggg agt gtg gca cca ggc ccc ctg agc<br>Asn Gln Tyr Asn Pro Leu Arg Gly Ser Val Ala Pro Gly Pro Leu Ser<br>          690                          695                          700 | 2112 |
| aca cag gcc ccc tcc ctg cag cat ggc atg gta ggc ccg ctg cac agt<br>Thr Gln Ala Pro Ser Leu Gln His Gly Met Val Gly Pro Leu His Ser<br>705                          710                          715                          720 | 2160 |

```
agc ctt gct gcc agc gcc ctg tcc cag atg atg agc tac cag ggc ctg     2208
Ser Leu Ala Ala Ser Ala Leu Ser Gln Met Met Ser Tyr Gln Gly Leu
            725                 730                 735 ccc agc acc cgg ctg gcc acc cag cct cac ctg gtg cag acc cag cag     2256
Pro Ser Thr Arg Leu Ala Thr Gln Pro His Leu Val Gln Thr Gln Gln
        740                 745                 750 gtg cag cca caa aac tta cag atg cag cag cag aac ctg cag cca gca     2304
Val Gln Pro Gln Asn Leu Gln Met Gln Gln Gln Asn Leu Gln Pro Ala
    755                 760                 765 aac atc cag cag cag caa agc ctg cag ccg cca cca cca cca cag         2352
Asn Ile Gln Gln Gln Gln Ser Leu Gln Pro Pro Pro Pro Pro Gln
770                 775                 780 ccg cac ctt ggc gtg agc tca gca gcc agc ggc cac ctg ggc cgg agc     2400
Pro His Leu Gly Val Ser Ser Ala Ala Ser Gly His Leu Gly Arg Ser
785                 790                 795                 800 ttc ctg agt gga gag ccg agc cag gca gac gtg cag cca ctg ggc ccc     2448
Phe Leu Ser Gly Glu Pro Ser Gln Ala Asp Val Gln Pro Leu Gly Pro
                805                 810                 815 agc agc ctg gcg gtg cac act att ctg ccc cag gag agc ccc gcc ctg     2496
Ser Ser Leu Ala Val His Thr Ile Leu Pro Gln Glu Ser Pro Ala Leu
            820                 825                 830 ccc acg tcg ctg cca tcc tcg ctg gtc cca ccc gtg acc gca gcc cag     2544
Pro Thr Ser Leu Pro Ser Ser Leu Val Pro Pro Val Thr Ala Ala Gln
        835                 840                 845 ttc ctg acg ccc ccc tcg cag cac ags tac tcc tyg cct gtg gac aac     2592
Phe Leu Thr Pro Pro Ser Gln His Xaa Tyr Ser Xaa Pro Val Asp Asn
    850                 855                 860 acc ccc agc cac cag cta cag gtg cct gag cac ccc ttc ctc acc ccg     2640
Thr Pro Ser His Gln Leu Gln Val Pro Glu His Pro Phe Leu Thr Pro
865                 870                 875                 880 tcc cct gag tcc cct gac cag tgg tcc agc tyg tcc ccg cat tcc aac     2688
Ser Pro Glu Ser Pro Asp Gln Trp Ser Ser Xaa Ser Pro His Ser Asn
                885                 890                 895 gtc tcc gac tgg tcc gag ggc gtc tcc agc cct ccc acc agc atg cag     2736
Val Ser Asp Trp Ser Glu Gly Val Ser Ser Pro Pro Thr Ser Met Gln
            900                 905                 910 tcc cag atc gcc cgc att ccg gag gcc ttc aag taa                     2772
Ser Gln Ile Ala Arg Ile Pro Glu Ala Phe Lys
        915                 920
```

<210> SEQ ID NO 6
<211> LENGTH: 923
<212> TYPE: PRT
<213> ORGANISM: Artificial Sequence
<220> FEATURE:
<221> NAME/KEY: misc_feature
<222> LOCATION: (857)..(857)
<223> OTHER INFORMATION: The 'Xaa' at location 857 stands for Arg, or
      Ser.
<220> FEATURE:
<221> NAME/KEY: misc_feature
<222> LOCATION: (860)..(860)
<223> OTHER INFORMATION: The 'Xaa' at location 860 stands for Ser, or
      Leu.
<220> FEATURE:
<221> NAME/KEY: misc_feature
<222> LOCATION: (891)..(891)
<223> OTHER INFORMATION: The 'Xaa' at location 891 stands for Ser, or
      Leu.
<220> FEATURE:
<223> OTHER INFORMATION: Synthetic Construct

<400> SEQUENCE: 6

Met Pro Pro Leu Leu Ala Pro Leu Leu Cys Leu Ala Leu Leu Pro Ala

```
1               5                   10                  15
Leu Ala Ala Arg Gly Pro Arg Gly Ser Ile Val Tyr Leu Glu Ile Asp
                20                  25                  30

Asn Arg Gln Cys Val Gln Ala Ser Ser Gln Cys Phe Gln Ser Ala Thr
            35                  40                  45

Asp Val Ala Ala Phe Leu Gly Ala Leu Ala Ser Leu Gly Ser Leu Asn
        50                  55                  60

Ile Pro Tyr Lys Ile Glu Ala Val Gln Ser Glu Thr Val Glu Pro Pro
65                  70                  75                  80

Pro Pro Ala Gln Leu His Phe Met Tyr Val Ala Gln Ala Val Glu Pro
                85                  90                  95

Pro Pro Pro Ala Gln Leu His Phe Met Tyr Val Ala Ala Ala Ala Phe
                100                 105                 110

Val Leu Leu Phe Phe Val Gly Cys Gly Val Leu Leu Ser Arg Lys Arg
                115                 120                 125

Arg Arg Gln His Gly Gln Leu Trp Phe Pro Glu Gly Phe Lys Val Ser
        130                 135                 140

Glu Ala Ser Lys Lys Lys Arg Arg Glu Pro Leu Gly Glu Asp Ser Val
145                 150                 155                 160

Gly Leu Lys Pro Leu Lys Asn Ala Ser Asp Gly Ala Leu Met Asp Asp
                165                 170                 175

Asn Gln Asn Glu Trp Gly Asp Glu Asp Leu Glu Thr Lys Lys Phe Arg
                180                 185                 190

Phe Glu Glu Pro Val Val Leu Pro Asp Leu Asp Asp Gln Thr Asp His
            195                 200                 205

Arg Gln Trp Thr Gln Gln His Leu Asp Ala Ala Asp Leu Arg Met Ser
        210                 215                 220

Ala Met Ala Pro Thr Pro Gln Gly Glu Val Asp Ala Asp Cys Met
225                 230                 235                 240

Asp Val Asn Val Arg Gly Pro Asp Gly Phe Thr Pro Leu Met Ile Ala
                245                 250                 255

Ser Cys Ser Gly Gly Gly Leu Glu Thr Gly Asn Ser Glu Glu Glu Glu
                260                 265                 270

Asp Ala Pro Ala Val Ile Ser Asp Phe Ile Tyr Gln Gly Ala Ser Leu
            275                 280                 285

His Asn Gln Thr Asp Arg Thr Gly Glu Thr Ala Leu His Leu Ala Ala
        290                 295                 300

Arg Tyr Ser Arg Ser Asp Ala Ala Lys Arg Leu Leu Glu Ala Ser Ala
305                 310                 315                 320

Asp Ala Asn Ile Gln Asp Asn Met Gly Arg Thr Pro Leu His Ala Ala
                325                 330                 335

Val Ser Ala Asp Ala Gln Gly Val Phe Gln Ile Leu Ile Arg Asn Arg
                340                 345                 350

Ala Thr Asp Leu Asp Ala Arg Met His Asp Gly Thr Thr Pro Leu Ile
            355                 360                 365

Leu Ala Ala Arg Leu Ala Val Glu Gly Met Leu Glu Asp Leu Ile Asn
        370                 375                 380

Ser His Ala Asp Val Asn Ala Val Asp Asp Leu Gly Lys Ser Ala Leu
385                 390                 395                 400

His Trp Ala Ala Ala Val Asn Asn Val Asp Ala Ala Val Val Leu Leu
                405                 410                 415

Lys Asn Gly Ala Asn Lys Asp Met Gln Asn Asn Arg Glu Glu Thr Pro
                420                 425                 430
```

```
Leu Phe Leu Ala Ala Arg Glu Gly Ser Tyr Glu Thr Ala Lys Val Leu
        435                 440                 445

Leu Asp His Phe Ala Asn Arg Asp Ile Thr Asp His Met Asp Arg Leu
    450                 455                 460

Pro Arg Asp Ile Ala Gln Glu Arg Met His His Asp Ile Val Arg Leu
465                 470                 475                 480

Leu Asp Glu Tyr Asn Leu Val Arg Ser Pro Gln Leu His Gly Ala Pro
                485                 490                 495

Leu Gly Gly Thr Pro Thr Leu Ser Pro Pro Leu Cys Ser Pro Asn Gly
                500                 505                 510

Tyr Leu Gly Ser Leu Lys Pro Gly Val Gln Gly Lys Lys Val Arg Lys
            515                 520                 525

Pro Ser Ser Lys Gly Leu Ala Cys Gly Ser Lys Glu Ala Lys Asp Leu
            530                 535                 540

Lys Ala Arg Arg Lys Lys Ser Gln Asp Gly Lys Gly Cys Leu Leu Asp
545                 550                 555                 560

Ser Ser Gly Met Leu Ser Pro Val Asp Ser Leu Glu Ser Pro His Gly
                565                 570                 575

Tyr Leu Ser Asp Val Ala Ser Pro Pro Leu Leu Pro Ser Pro Phe Gln
                580                 585                 590

Gln Ser Pro Ser Val Pro Leu Asn His Leu Pro Gly Met Pro Asp Thr
            595                 600                 605

His Leu Gly Ile Gly His Leu Asn Val Ala Ala Lys Pro Glu Met Ala
    610                 615                 620

Ala Leu Gly Gly Gly Gly Arg Leu Ala Phe Glu Thr Gly Pro Pro Arg
625                 630                 635                 640

Leu Ser His Leu Pro Val Ala Ser Gly Thr Ser Thr Val Leu Gly Ser
                645                 650                 655

Ser Ser Gly Gly Ala Leu Asn Phe Thr Val Gly Gly Ser Thr Ser Leu
            660                 665                 670

Asn Gly Gln Cys Glu Trp Leu Ser Arg Leu Gln Ser Gly Met Val Pro
        675                 680                 685

Asn Gln Tyr Asn Pro Leu Arg Gly Ser Val Ala Pro Gly Pro Leu Ser
    690                 695                 700

Thr Gln Ala Pro Ser Leu Gln His Gly Met Val Gly Pro Leu His Ser
705                 710                 715                 720

Ser Leu Ala Ala Ser Ala Leu Ser Gln Met Met Ser Tyr Gln Gly Leu
                725                 730                 735

Pro Ser Thr Arg Leu Ala Thr Gln Pro His Leu Val Gln Thr Gln Gln
            740                 745                 750

Val Gln Pro Gln Asn Leu Gln Met Gln Gln Asn Leu Gln Pro Ala
            755                 760                 765

Asn Ile Gln Gln Gln Gln Ser Leu Gln Pro Pro Pro Pro Pro Gln
770                 775                 780

Pro His Leu Gly Val Ser Ser Ala Ala Ser Gly His Leu Gly Arg Ser
785                 790                 795                 800

Phe Leu Ser Gly Glu Pro Ser Gln Ala Asp Val Gln Pro Leu Gly Pro
                805                 810                 815

Ser Ser Leu Ala Val His Thr Ile Leu Pro Gln Glu Ser Pro Ala Leu
            820                 825                 830

Pro Thr Ser Leu Pro Ser Ser Leu Val Pro Val Thr Ala Ala Gln
            835                 840                 845
```

```
Phe Leu Thr Pro Pro Ser Gln His Xaa Tyr Ser Xaa Pro Val Asp Asn
            850                 855                 860

Thr Pro Ser His Gln Leu Gln Val Pro Glu His Pro Phe Leu Thr Pro
865                 870                 875                 880

Ser Pro Glu Ser Pro Asp Gln Trp Ser Xaa Ser Pro His Ser Asn
                885                 890                 895

Val Ser Asp Trp Ser Glu Gly Val Ser Ser Pro Pro Thr Ser Met Gln
            900                 905                 910

Ser Gln Ile Ala Arg Ile Pro Glu Ala Phe Lys
            915                 920

<210> SEQ ID NO 7
<211> LENGTH: 22
<212> TYPE: DNA
<213> ORGANISM: Artificial Sequence
<220> FEATURE:
<223> OTHER INFORMATION: sh oligonucleotide for mouse RPL10

<400> SEQUENCE: 7
aaccgacgat cctattgtca tc                                          22

<210> SEQ ID NO 8
<211> LENGTH: 20
<212> TYPE: DNA
<213> ORGANISM: Artificial Sequence
<220> FEATURE:
<223> OTHER INFORMATION: RPL10 targeting gRNA

<400> SEQUENCE: 8
tcttgttgat gcggatgacg                                             20

<210> SEQ ID NO 9
<211> LENGTH: 130
<212> TYPE: DNA
<213> ORGANISM: Artificial Sequence
<220> FEATURE:
<223> OTHER INFORMATION: gRNA-Cas9 complex

<400> SEQUENCE: 9
cctgtcagcc ccagcacagg acaacatctt gttaatgctg atcacgtgaa aggggtggag     60
ccgcacccgg atatggaagc catctttgcc acaacttttt accatgtact tattggcaca    120
aattcgggca                                                          130

<210> SEQ ID NO 10
<211> LENGTH: 19
<212> TYPE: DNA
<213> ORGANISM: Artificial Sequence
<220> FEATURE:
<223> OTHER INFORMATION: RPL10 WT specific forward primer

<400> SEQUENCE: 10
cttccacgtc atccgcatc                                              19

<210> SEQ ID NO 11
<211> LENGTH: 20
<212> TYPE: DNA
<213> ORGANISM: Artificial Sequence
<220> FEATURE:
<223> OTHER INFORMATION: RPL10 R98S specific forward primer

<400> SEQUENCE: 11
cctttcacgt gatcagcatt                                             20
```

```
<210> SEQ ID NO 12
<211> LENGTH: 25
<212> TYPE: DNA
<213> ORGANISM: Artificial Sequence
<220> FEATURE:
<223> OTHER INFORMATION: RPL10 reverse primer

<400> SEQUENCE: 12
gctctgataa ataatgcaa gccta                                          25
```

RECOMBINANT PROTEIN PRODUCTION SYSTEM

FIELD OF THE INVENTION

The present disclosure relates generally to an improved protein expression system in the field of recombinant protein expression. The invention relates to a system showing an improved yield and quality of protein production and methods for increasing production of a protein produced by cultured cells, particularly cultured eukaryotic cells.

BACKGROUND

Improved methodologies for maximizing protein production through recombinant gene expression is an on-going effort in the art. Of particular interest is the development of methodologies that maximize recombinant expression of biologically active proteins for producing commercially useful quantities of these proteins. While prokaryotic, typically bacterial, host cell systems have proven capable of generating large quantities of recombinant proteins, these hosts suffer from a number of disadvantages, including an inability to glycosylate proteins, inefficient cleavage of "pre" or "prepro" sequences from proteins (e.g., inefficient post translational modification), and a general inability to secrete proteins. Consequently the art has sought eukaryotic host systems, typically mammalian host cell systems, for mammalian protein production. One feature of such systems is that the protein produced has a structure most like that of the natural protein species, and, purification often is easier since the protein can be secreted into the culture medium in a biologically active form.

Proteins are commercially useful in a large variety of applications, including diagnostic, pharmacological, therapeutic, nutritional, and research applications. Large scale production of proteins for commercial use can be both laborious and expensive. Moreover, facilities that produce proteins for pharmacological use can incur significant cost to obtain building and regulatory approval. Thus, even small increases in the efficiency with which a protein can be produced are commercially valuable because of the limited number of facilities available for production and the expense of production.

Cultured mammalian cells have been used for production of some proteins, particularly recombinant proteins intended for pharmacological use, and numerous adjustments of culture conditions have been shown to affect the quantity and quality of protein produced.

Chen et al. (2006) *Appl Environ Microbiol.* 72, 4001-4006 identified a tomato (*Lycopersicon esculentum*) gene encoding a QM-like protein (tQM) and found that stable expression of tQM conferred protection against oxidative damage from H2O2, paraquat, and heat. The same authors disclose in US20080184384 an eukaryote expression system with QM overexpression to increase the yield of a recombinant protein due to a reduced stress tolerance. The QM protein has homologues in yeast and vertebrates. The human homologue is known as RPL10. De Keersmaecker K. et al. (2013) *Nat Genet.* 45, 186-190 identify mutations in the ribosomal gene RPL10 in T-cell acute lymphoblastic leukaemia.

SUMMARY OF THE INVENTION

The present invention provides a new system that is designed to improve the yield and quality of protein production, particularly a recombinant protein, from cultured eukaryotic, in particular mammalian cells.

Although engineered RPL10 eukaryotic cells show a ribosome biogenesis defect, the present invention solves the problems of the related art by increasing translation efficiency and translation fidelity, thereby providing a system with an improved yield and quality of protein production.

The invention is summarized in the following statements:

1. A method for producing a second recombinant protein said method comprising providing an eukaryotic host cell expressing a mutant RPL10 protein, wherein wild type RPL10 is not expressed or its expression is silenced within said eukaryotic cell, and introducing a nucleic acid encoding a recombinant protein under conditions that allow expression of the recombinant polypeptide.

2. The method according to statement 1, further comprising the step of recovering the expressed polypeptide from the host cell.

3. The method according to statement 1 or 2, wherein endogenous RPL10 DNA sequence has been deleted from the genome, wherein the expression of endogenous RPL10 has been silenced or wherein the endogenous RPL10 DNA sequence has been altered to encode the mutant RPL10.

4. The method according to any one of statements 1 to 3, wherein mutant RPL10 protein comprises one or more amino acids substitutions at positions 33, 66, 70, 98, 123 or an equivalent mutation at another position in the protein leading to increased expression of a recombinant protein.

5. The method according to any one of statements 1 to 4, wherein mutant RPL10 protein comprises one or more amino acids substitutions at positions 33, 66, 70, 98, and 123.

6. The method according to any one of statements 1 to 5, wherein mutant RPL10 protein comprises one or more amino acids substitutions at selected from the group consisting of 33Val, 66Gly, 70Met or 70Leu, 98Ser or 98Cys, and 123 Pro.

7. The method according to any one of statements 1 to 6, wherein the mutant RPL10 protein contains the mutation 98Ser.

8. The method according to any one of statements 1 to 7, wherein the cells are grown in a medium comprising an antioxidant.

9. The method according to any one of statements 1 to 8, wherein NOTCH1 signalling is activated in the host cells.

10. The method according to statement 9, wherein NOTCH1 signalling is activated by transduction with a retroviral vector harbouring MSCV plasmids encoding activated intracellular NOTCH1 (NOTCH1-ICN) for example as shown in SEQ ID NO:5.

11. The method according to any one of statements 1 to 10, wherein the recombinant eukaryotic cell host is a mammalian cell.

12. The method according to statement 11, wherein the mammalian cell is a cell line selected from the group consisting of CHO, COS, Vero, Hela, BHK, HEK293, Hek293T, HKB-11, MEF and Sp-2 cell lines.

13. Use of an eukaryotic cell expressing a mutant RPL10 protein, wherein wild type RPL10 is not expressed or its expression is silenced within said eukaryotic cell for the expression of recombinant proteins.

14. A eukaryotic cell expressing a mutant RPL10 protein, wherein wild type RPL10 is not expressed or its expression is silenced within said eukaryotic cell, characterized by activated NOTCH1 signalling.

15. The cell according to statement 14, comprising intracellular NOTCH1 (NOTCH1-ICN) for example as shown in SEQ ID NO:5].

16. A method for identifying RPL10 mutations which results in increased expression of a recombinant protein in a cell comprising such RPL10 compared to a cell comprising wild type RPL10, introducing in a first cell a first nucleic acid encoding a mutated RPL10 protein under conditions that allow expression of the mutated, wherein wild type RPL10 is absent, introducing in said first cell a second nucleic acid encoding a detectable protein under conditions that allow expression of the detectable protein.

introducing in a second cell a third nucleic acid encoding a wild type RPL10 protein under conditions that allow expression of the mutated, introducing in said second cell the second nucleic acid encoding the detectable protein under conditions that allow expression of the detectable protein.

Cultivating the first cell and the second cell under the same conditions and comparing the amount of detectable protein produced, wherein a cell with an RPL10 mutant wherein an increase of at least 2% (w/w) of detectable protein is obtained, is selected as host for the expression of recombinant proteins.

17. Use of a cell selected in the method of statement 16, in a method according to statement 1.

18. A non-human transgenic animal expressing a R98S RPL10 mutation.

19. The non-human transgenic animal according to statement 18, which is a conditional transgenic animal expressing the R98S RPL10 mutation via CRE-recombinase.

20. The non-human transgenic animal according to statement 18 or 19, wherein the R98S RPL10 mutation is tissue specific.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF DRAWINGS

The present invention will become more fully understood from the detailed description given herein below and the accompanying drawings which are given by way of illustration only, and thus are not limitative of the present invention, and wherein:

FIG. 1 is a schematic overview of Programmed −1 ribosomal frameshifting (−1 PRF) assays. Wild type and mutant Ba/F3 cells were mock-electroporated or electroporated with plasmids harbouring the in frame control, the out of frame control, or a −1 PRF signal from the human IL7R gene between the upstream renilla and downstream firefly luciferase open reading frames.

FIG. 2 is a schematic overview of nonsense and missense suppression analysis. Nonsense suppression analysis is carried out via a dual luciferase assay wherein a STOP codon is introduced between the renilla and firefly luciferase genes. In such a construct, the production of the firefly luciferase protein is dependent on a STOP codon read-through event. Missense suppression is assayed by employing a construct containing the R218S single base substitution in the firefly luciferase active site. In such a construct, the activity of firefly luciferase is dependent on the incorporation of a near-cognate arginine instead of a cognate serine.

FIG. 4 shows that RPL10 R98S cells have a higher translation accuracy. Results from dual luciferase reporter assays testing −1 PRF levels (frameshifting), STOP codon read-trough and missense reading in Ba/F3 cells expressing WT or RPL10 R98S. ** p<0.01

FIG. 5 illustrates that RPL10 R98S cells show reduced chymotrypsin-like and caspase-like protease activity. Chymotrypsin-Like, Trypsin-Like and Caspase-Like proteasomal activity of Ba/F3 (top) or Jurkat (bottom) cells expressing either WT or R98S RPL10. P-values were calculated using a T-test.

FIG. 6 illustrates that NOTCH1-ICN signalling rescues RPL10 R98S associated cell proliferation defects without affecting translation fidelity. A) Proliferation curves of Ba/F3 cells expressing indicated constructs. B) Results from dual luciferase reporter assays testing −1 PRF levels (frameshifting), STOP codon read-trough and missense reading in cells expressing indicated constructs.

FIG. 12 shows that the Jak-Stat pathway genes contain functional −1 PRF signals, the frameshifting levels on some of which are influenced by the RPL10 R98S mutation. A) Results of enrichment analysis within all human genes containing predicted −1 PRF signals and extracted from the PRF database (Belew A T. et al. (2008) *BMC Genomics* 9, 339). Analysis was performed using the G:profiler (Reimand, J. et al. (2016) *Nucleic Acids Res* 44, W83-W89) software and KEGG databases, and statistical significance was calculated using Fisher's one-tailed test. B) Results from dual luciferase reporter assays (explained in FIG. 18A) testing −1 PRF levels on computationally predicted −1 PRF signals in the indicated mouse genes. The out-of-frame (OOF) is a negative control. Assays were performed in Ba/F3 cells expressing RPL10 WT or R98S. The bars indicate the average+/−standard error of at least 5 biologically independent measurements. C) Percentages of −1 PRF on human IL7RA and JAK1 mRNAs as determined by dual luciferase reporter assays performed in WT versus R98S Ba/F3 cells. Plots show the average+/−standard error of at least 5 biologically independent measurements.

FIG. 16 illustrates that RPL10 R98S mouse hematopoietic cells show upregulation of immunoproteasome subunits. Representative immunoblots showing protein expression levels of the specific subunits Psmb10 and Psmb9 of the immunoproteasome in hematopoietic cells derived from Rpl10$^{cKI\ R98S}$ (labelled as WT in the figure) and MX-Cre Rpl10$^{cKI\ R98S}$ (labelled as R98S in the figure) mice.

FIG. 17 shows that RPL10 R98S mutant cells do not show altered poly-ubiquitination. A) Immunoblot analysis of poly-ubiquitinated proteins in RPL10 R98S versus WT expressing Ba/F3 cells. The figure shows a representative blot of 3 independent experiments. B) Quantification of the immunoblots of panel (A). The plot shows the average+/−st dev.

FIG. 19 shows an alignment of human, mouse and yeast RPL10, with indication of the mutations discussed in the application.

DETAILED DESCRIPTION

Figure 3:
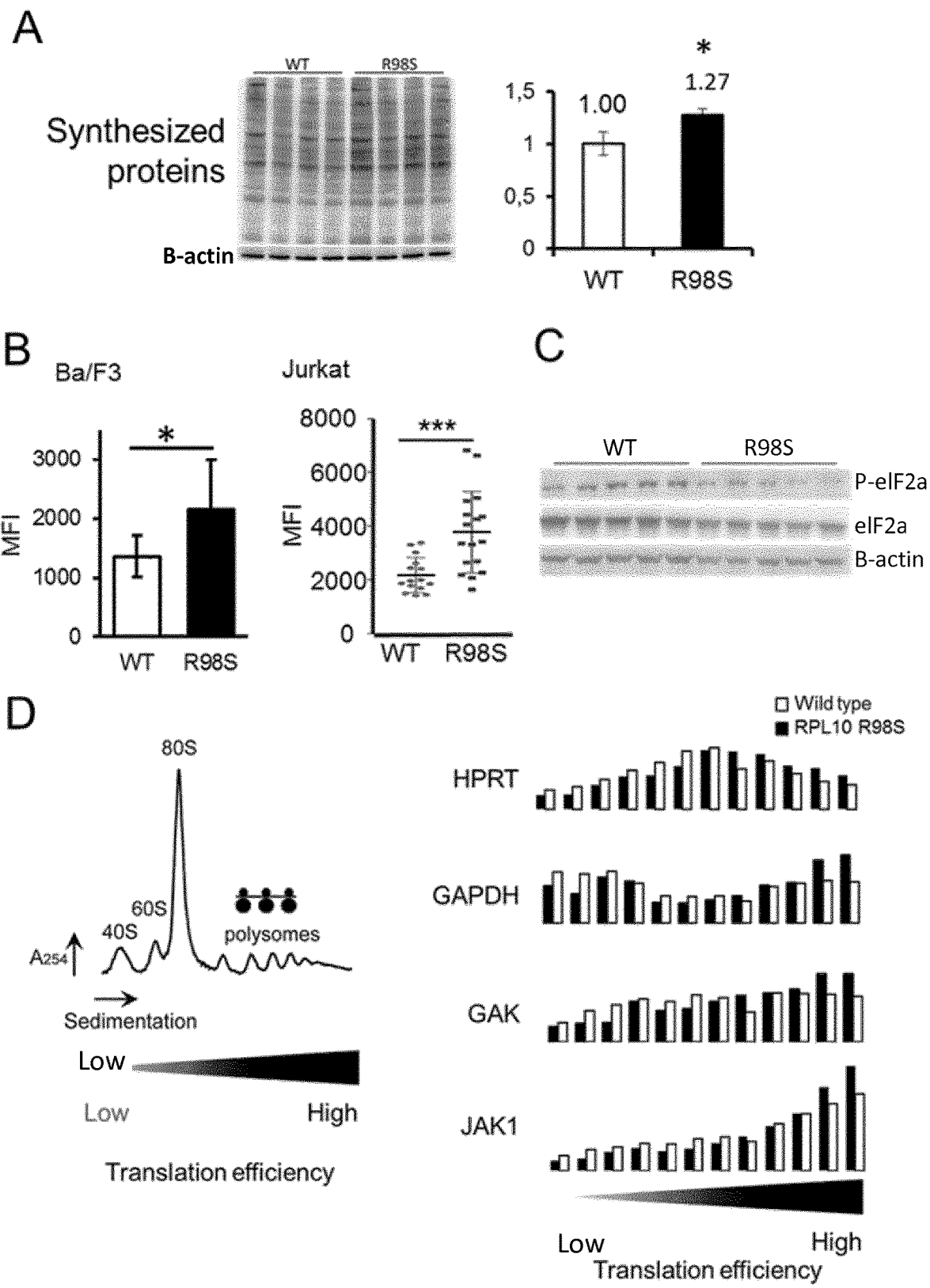
FIG. 3 shows increased translation efficiency in RPL10 R98S cells A) Representative western blot analysis of de novo protein labelling with AHA-Biotin detected with streptavidin-HRP antibody (*: p<0.05; T-test) on Ba/F3 WT versus R98S cells. B) Comparison of MFI (mean fluorescent intensity) of a GFP reporter expressed in RPL10 R98S versus WT expressing cells. Left: Ba/F3 cells; Right: Jurkat cells C) Representative western blot detection of phospho-eIF2α in RPL10 WT and R98S expressing Ba/F3 cells. D) Analysis of the distribution of indicated mRNAs in polysome profiles from RPL10 WT and R98S Ba/F3 expressing cells.

The present disclosure relates generally to an improved protein expression system in the field of recombinant protein expression. The invention relates to methods for increasing production of a protein produced by cultured cells, particularly cultured eukaryotic cells.

Several somatic ribosome defects have recently been discovered in cancer, yet their underlying oncogenic mechanisms remain poorly understood. Here we investigated the pathogenic role of the recurrent R98S mutation in the essential ribosomal protein L10 (RPL10) found in T-cell acute lymphoblastic leukaemia (T-ALL). In our T-ALL patient cohorts, the arginine to serine mutation at position 98 (R98S) in RPL10 (also known as µL16) was by far the most recurrent ribosomal defect, detected in 7.9% of paediatric patients. The R98 residue of RPL10 is centrally situated in the 60S subunit and closely approaches the ribosomal catalytic core. Yeast models have revealed that the RPL10 R98S mutation impairs ribosome assembly, translational fidelity, and cell proliferation. Although recombinant RPL10 eukaryotic cells show a ribosome biogenesis defect, they do exhibit enhanced survival properties in nutrient poor conditions and an improved yield and quality of protein production. Therefore the present invention solves the problems of the related art by increasing translation efficiency and translation fidelity, thereby providing a system showing an improved protein production.

The term "recombinant" as used herein refers to a product such as DNA or protein originating from combining genetic material from two or more different sources by means of genetic engineering.

"recombinant expression system" refers to any nucleic acid based approach or system for the expression of a gene product or gene products of interest, that has been artificially organized (man-made) of components directed toward the expression of the gene product or products. The components may be of naturally occurring genetic sources, synthetic or artificial, or some combination of natural and artificial genetic elements. Generally the gene product is a protein, polypeptide, or peptide.

A "recombinant protein" may be identical to a protein already expressed by the host cell, may be a mutated version and/or fragments of a protein already expressed by the host cell, or may be a protein (wild type of modified) origination from another organism. Recombinant proteins may further comprise additional elements such as tags or fusion parts for isolation and identification (e.g. fluorescent proteins) or other modifications.

Specific recombinant proteins in the context of the present invention are proteins with post-translational modifications such as glycosylated proteins, proteins with disulphide proteins, and the like.

Since the mutant RPL10 is a recombinant protein, the protein on the expression vector is referred to as a "further" or a second recombinant protein.

"Heterologous DNA sequence" refers to any DNA sequence that is foreign or not naturally associated with the other DNA sequences to which it is associated or linked (operably or otherwise), or a DNA sequence that is not naturally associated with the cell or organism into which it is introduced. An example of a heterologous DNA sequence is one that is used for the expression of a foreign or heterologous protein gene product in a host cell or organism. A heterologous DNA sequence can also be a part of a vector or expression construct having genetic material designed for directing the expression of a gene product, such as a protein, polypeptide, or peptide, in a host cell in vivo or in vitro, or in a cell free in vitro expression system.

Disclosed herein are:

Recombinant eukaryotic cell clones comprising a recombinant DNA sequence encoding mutant RPL10, wherein said cells expresses said mutant RPL10 and wherein the expression of the endogenous RPL10 DNA sequence has been deleted from the genome or wherein the expression of said endogenous RPL10 has been silenced or wherein the endogenous RPL10 DNA sequence has been altered to encode the mutant RPL10.

Typically said recombinant DNA sequence encodes a mutant RPL10 protein comprising one or more amino acid substitutions selected from the group consisting of I33V, E66G, I70M, I70L, R98S, R98C, H123P and Q123P as compared to for instance the consensus RPL10 protein sequences SEQ ID NO:2 (human), SEQ ID NO:3 (mouse), SEQ ID NO:4 (yeast) or homologues thereof. Specifically, in the recombinant DNA sequence encoding mutant RPL10 the nucleotide triplet encoding amino acid 98 has been replaced with a triplet encoding serine.

In these eukaryotic cell clones, NOTCH1 signalling may be additionally activated by transduction with activated intracellular NOTCH1. for example with a retroviral vector harbouring MSCV plasmids encoding activated intracellular NOTCH1 (NOTCH1-ICN) such as shown in SEQ ID NO:5. Indeed, NOTCH1 is a transmembrane protein whereby the released intracellular part can migrate to the nucleus where it functions as a transcription factor. Constructs such as the one depicted in SEQ ID NO:6 are active as such since they are independent of NOTCH proteolytic processing.

The intracellular domain of NOTCH 1 is encoded by nucleotides 5260 to 7665 of NOTCH 1 as depicted in NCBI Reference Sequence: NM_017617.4 (version Nov. 12, 2017). An embodiment of a protein sequence comprising the intracellular domain of NOTCH 1 is shown SEQ ID NO:6, wherein the sequence of the intracellular domain is underlined. The double underlined sequence are the 22 N terminal amino acids of Notch 1.

The eukaryotic cell line is for example a mammalian cell line selected from the group consisting of CHO, COS, Vero, Hela, BHK, HEK293, Hek293T, Hek293S, Hek293FT, HKB-11, MEF and Sp-2 cell lines Herein disclosed are also methods of producing the recombinant eukaryotic cell clones described in the above paragraphs via a CRISPR-CAS9 system comprising stably or transiently transfecting eukaryotic cell lines with a Cas9 expression construct or Cas9 protein and transfecting with a gRNA targeting Rpl10 and with a donor oligo encoding the mutation selected from the group consisting of I33V, E66G, I70M, I70L, R98S, R98C, H123P and Q123P as shown in SEQ ID NO:2 for human, SEQ ID NO:3 for mouse, and SEQ ID NO:4 for yeast.

Herein disclosed are also methods of producing the recombinant eukaryotic cell clones described in the above paragraphs via transduction with a retroviral vector encoding mutant RPL10 and knocking down endogenously expressed Rpl10 by transduction with an Rpl10 targeting shRNA construct as shown in SEQ ID NO:6.

Herein disclosed are also methods of producing the recombinant eukaryotic cell clones described in the above paragraphs via a CRISPR-Cas9 system comprising stably or transiently transfecting eukaryotic cell lines with a Cas9 expression construct or Cas9 protein and transfecting with a gRNA targeting Rpl10 and with a donor oligo encoding the mutation selected from the group consisting of I33V, E66G, I70M, I70L, R98S, R98C, H123P and Q123P wherein additionally NOTCH1 signalling is activated by transduction with a retroviral vector harbouring MSCV plasmids encoding the active cleaved form of Notch1.

Herein disclosed are also methods of producing the recombinant eukaryotic cell clones described in the above paragraphs, via retroviral vector encoding the RPL10 mutant selected from the group consisting of I33V, E66G, I70M, I70L, R98S, R98C, H123P and Q123P, wherein endogenously expressed Rpl10 is knocked down by transduction with an Rpl10 targeting shRNA construct as shown in SEQ ID NO:7 and wherein additionally NOTCH1 signalling is activated by transduction with a retroviral vector harbouring MSCV plasmids encoding the active cleaved form of Notch1

In these methods of producing the recombinant eukaryotic cell clone the mutation is typically R98S.

Herein disclosed are methods for producing a second recombinant protein other than RPL10 said method comprising culturing a recombinant eukaryotic cell clone as described in the above paragraphs that has been transfected with a second recombinant DNA sequence encoding said second recombinant protein of interest and recovering the second protein so produced.

Herein disclosed are methods for increasing the protein production efficiency of an eukaryotic cell clone wherein said method comprises transforming said eukaryotic cell clone using any of the methods described above.

The present invention relates to expression systems using a host cell comprising a mutant RPL10, typically mutated at one or more of positions 33, 66, 70, 98, and 123 with reference to the numbering of human RPL10 shown in FIG. 19. Mutations are for example mutations at position 33 e.g. into Val, Leu, Met, at position 66 into e.g. Gly, Ala, Ser, Thr, Cys, at position 70 e.g. into Val, Leu, Met, at position 98 into e.g. Gly, Ala, Ser, Thr, Cys.

More specific mutations are Ile33Val, Glu66Gly, Ile70Met or Ile70Leu, Arg98Ser, Arg98Cys, Gln/His123Pro.

Equivalents are mutations of RPL10 other than Ile33Val, Glu66Gly, Ile70Met or Ile70Leu, Arg98Ser, Arg98Cys, Gln/His123Pro, which lead to an increased overexpression of a recombinant protein. This can be tested by comparing the expression of a recombinant protein in a cell transfected with wild type RPL10 versus a cell transfected the mutant RPL10. Apart from point mutant, deletions of one more amino acids at the N terminus, C terminus and internally in the sequence are envisaged.

In host cells, the endogenous wild type RPL10 is mutated into one or more of the mutations Ile33Val, Glu66Gly, Ile70Met or Ile70Leu, Arg98Ser, Arg98Cys, 123Pro or an equivalent. Alternatively the wild type RPL10 is inactivated by silencing or by complete or partial deletion of the wild type RPL10 gene and an expression construct encoding RPL10 with mutations Ile33Val, Glu66Gly, Ile70Met or Ile70Leu, Arg98Ser, Arg98Cys, 123Pro or an equivalent is introduced. "Equivalents" are those mutations which lead to an increased expression as determined in the above described method.

The methods of recombinant expression can be performed in a variety of eukaryotic cells including yeast cells (e.g. *saccharomyces, aspergillus, Pichia*, insect cells, algae, plant cells and plants, mammalian cells (e.g. rodent, non-human primates, human). Specific embodiments are expression systems other than yeast. Commercial expression systems are available and the host cells are amenable for modifications such as transfection of a transgene RPL10 construct and the inactivation or mutation of endogenous RPL10, especially in view of the emerging Crisp/Cas technology.

The highly conserved ribosomal machinery and the high sequence similarity of RPL10 between unrelated organisms make it likely that e.g. expression of mouse or even yeast mutant RPL10 in human cells may be as effective as expression of human mutant RPL10 in human cells in order to increase overexpression of a transgene. Typically RPL10 will be from the same organism as the host cell.

The mutant RPL10 may as mentioned be a mutant cell line as isolated from a patient or a cell line used for protein expression (such as CHO) wherein the wild type RPL10 is mutated. When the mutant RPL10 is introduced in a cell with a silenced or deleted RPL10, the mutant RPL10 may be integrated in the genome or may occur on a plasmid, viral vector, or any suitable vector for protein expression. The mutant RPL10 may be under the control of an inducible promotor, or may be constitutively expressed.

The invention relates to the use of a recombinant eukaryotic cell clone expressing a recombinant DNA molecule comprising a nucleotide sequence encoding a mutant RPL10.

Specific mutants of RPL10 are selected from any one of the group consisting of RPL10 I33V, RPL10 E66G, RPL10 I70M, RPL10 I70L, RPL10 R98C, and RPL10 R98S for mouse, yeast and human cells, RPL10 Q123P for mouse and human cells and RPL10 H123P for yeast cells.

In a specific embodiment, the recombinant eukaryotic cell clone expresses a recombinant DNA molecule comprising a nucleotide sequence encoding RPL10 as shown in SEQ ID NO:1 except that the nucleotide triplet encoding amino acid 98 has been replaced with a triplet encoding serine.

In specific embodiments of the invention, the recombinant RPL10 enhances survival properties in nutrient poor conditions and is combined with hyperactive NOTCH1 signalling to rescue the RPL10 associated cell proliferation defects without affecting the translation fidelity, therefore making such recombinant eukaryotic cells much more amenable for routine recombinant protein expression. Furthermore, the RPL10 R98S associated proliferation defect can be rescued by addition of antioxidants such as e.g. 5 mM N-acetyl-L-cysteine (NAC). A suitable alternative for NAC is for example glutathione.

The invention provides the recombinant RPL10 R98S cell clone, wherein additionally NOTCH1 signalling is activated by transduction with a retroviral vector harbouring MSCV plasmids encoding the active cleaved form of Notch1 as shown in SEQ ID NO:5.

The eukaryotic cell lines are conventional mammalian cell lines selected from the group consisting of CHO, COS, Vero, Hela, HEK 293, HEK 293T, BHK, HKB-11, MEF and Sp-2 cell lines. In another embodiment the eukaryotic cell line is derived from an animal model, expressing recombinant RPL10, e.g. MEF derived according to Lei (2013) *Methods Mol Biol* 1031:59-64.

The invention provides methods for producing the recombinant eukaryotic cell clone via a CRISPR-CAS9 system comprising stably or transiently transfecting eukaryotic cell lines with a Cas9 expression construct or Cas9 protein and transfecting with a gRNA targeting Rpl10 and with a donor oligo encoding the R98S modification.

The invention provides methods for producing the recombinant eukaryotic cell clone via transduction with a retroviral vector encoding R98S mutant RPL10 and knocking down endogenously expressed Rpl10 by transduction with an Rpl10 targeting shRNA construct as shown in SEQ ID NO:7.

The invention provides methods for producing the RPL10 R98S recombinant eukaryotic cell clone via a CRISPR- CAS9 system wherein additionally NOTCH1 signalling is activated by transduction with a retroviral vector harbouring MSCV plasmids encoding the active cleaved form of Notch1

The invention provides methods for producing the recombinant eukaryotic cell clone via retroviral vector encoding R98S mutant RPL10 and knocking down endogenously expressed Rpl10 by transduction with an Rpl10 targeting shRNA construct as shown in SEQ ID NO:7 and additionally activating NOTCH1 signalling.

The invention provides methods for producing a recombinant product comprising growing the recombinant eukaryotic cell clone that has been transfected with a protein of interest and recovering the protein so produced.

Particular and preferred aspects of the invention are set out in the accompanying independent and dependent claims. Features from the dependent claims may be combined with features of the independent claims and with features of other dependent claims as appropriate and not merely as explicitly set out in the claims.

Thus, the claims following the detailed description are hereby expressly incorporated into this detailed description, with each claim standing on its own as a separate embodiment of this invention.

EXAMPLES

Figure 14:
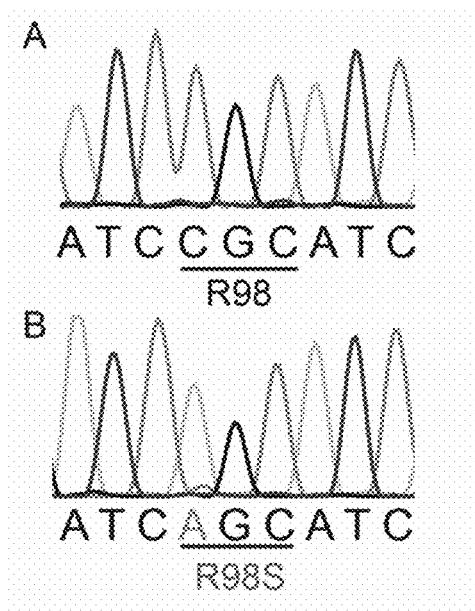
FIG. 14 shows Sanger sequences showing Rpl10 WT and R98S expression in Ba/F3 cells. Representative Sanger chromatogram of cDNA obtained from RPL10 WT (A) or R98S (B) expressing Ba/F3 cells.

Example 1: Generation of a Stable Cell Model Expressing the RPL10 R98S Mutation shRNA+Overexpression Model Mouse lymphoid pro-B cells (Ba/F3) were transduced with retroviral vectors encoding WT and R98S mutant RPL10 according to standard methods. These retroviral constructs were described previously (De Keersmaecker et al. (2013) cited above). T-ALL samples containing the RPL10 R98S defect only express mutant RPL10 (De Keersmaecker et al. (2013) cited above). To mimic this, endogenously expressed Rpl10 was knocked down in the Ba/F3 cell lines by transduction with an Rpl10 targeting shRNA construct. To generate this shRNA construct, a short hairpin RNA sequence (AACCGACGATCCTATTGTCATC: SEQ ID NO:7) targeting mouse Rpl10 was cloned into a mir30 cassette that was introduced into the pMSCV-Neo vector. In order to obtain cells with efficient and stable knock down of endogenous Rpl10, cultures were established from single cell colonies grown in Clonacell-TCS medium (Stemcell technologies). Only cultures with 90% or higher knock down of the endogenous Rpl10 as determined by qPCR were retained. Expression of RPL10 R98S and knock-down of endogenous Rpl10 were confirmed by Sanger sequencing of cDNA (FIG. 14).

CRISPR-Cas9 Model

In order to generate a stable CRISPR-Cas9 based model expressing the RPL10 R98S point mutation, Jurkat cells (DSMZ) were transduced with lentiCRISPR-Cas9, a lentiviral Cas9 encoding plasmid received from the laboratory of Prof. Jan Cools. These Jurkat cells were electroporated (6 square wave pulses, 0.1 ms interval, 175V) with a pX321 vector (Van der Krogt et al. (2017) Haematologica, 102, 1605-1616) containing an RPL10 targeting gRNA (5'-TCTTGTTGATG-CGGATGACG-3' [SEQ ID NO:8]) and with a 127-nt donor oligo containing the R98S allele as well as 3 silent mutations to avoid re-recognition and cutting by the gRNA-Cas9 complex (5'-CCTGTCAGC CCCAGC ACAGGACAACATCTT-GTTAATGCTGATCACGTGA AAGGGGTGGAGCCGCACCCGGATATGGAAGCCA TCTTTG CCACAAC ACCATGTACTTATTGGCACAAA TTCGGGCA-3' [SEQ ID NO:9]; Integrated DNA Technologies). Following electroporation, cells were incubated for 48 hrs in the presence of 500 nM SCR7 (Sigma-Aldrich), followed by single cell sorting (BD FACSAria I) into 96 well plates. Outgrowing clones were expanded and screened for the desired modification using a PCR approach. Since Rpl10 is located on the X chromosome and our Jurkat cells only contained one X chromosome, a PCR screen was done using allele specific primers (Fw_WT: 5'-CTTCCACGT-CATCCGCATC-3' [SEQ ID NO:10]; FW_R98S: 5'-CCTTTCACGT-GATCAGCATT-3' [SEQ ID NO:11]; Rev_WTandR98S: 5'-GCTCTGATAA-AATAATGCAA GCCTA-3' [SEQ ID NO:12]). Sanger sequencing was done to confirm the RPL10 status.

The exact same strategy is applicable to other human cell lines (e.g. Hek293 cells).

Subject to adaptions of the gRNA and donor oligo, mouse or hamster lines like Ba/F3, CHO can be generated.

Equally, depending on the Cas9 construct, transient Cas9 expression or transfection of Cas9 protein is possible.

Example 2: Metabolic Labelling Assay to Determine Levels of Freshly Synthesized Proteins Click-iT technology (Thermo Fisher Scientific) was employed to measure the levels of newly synthesized proteins in Ba/F3 cells. Briefly, 2 million cells were placed in methionine-free medium for 1 hour and then labelled for 2 hours with 35 µM AHA (L-azidohomoalanine). Cells were then lysed in lysis buffer (Cell Signalling Technology) and 100 µg of protein extract was used to perform the Click-iT biotin-conjugating reaction according to manufactures instruction. Subsequently, proteins were separated by gel electrophoresis and newly synthesized proteins were detected by immunoblot using a streptavidin-HRP antibody (Cell Signalling Technology).

Example 3: Analysis of GFP Expression

The plasmid used for expressing RPL10 WT or R98S in the Ba/F3 shRNA/overexpression model contains an IRES-GFP expression cassette. Expression levels of this cassette were monitored by measuring the mean fluorescent intensity (MFI) on a Guava Easycyte HT flow cytometer (Millipore). For the Jurkat RPL10 WT or R98S cells, a plasmid encoding a GFP expression cassette was electroporated and expression levels of this cassette were determined by measuring the mean fluorescent intensity (MFI) on a Guava Easycyte HT flow cytometer (Millipore) at 24 hours after electroporation.

Example 4: Polysomal Analysis

Ba/F3 cell pellets were lysed in ice-cold 100 mM KCl, 20 mM Hepes (Life technologies), 10 mM MgCl2, 1 mM DTT, 1% sodium deoxycholate, 1% NP-40 (Tergitol® solution, Sigma-Aldrich), 100 µg ml-1 cycloheximide, 1% Phosphatase Inhibitor Cocktail 2 (Sigma-Aldrich), 1% Phosphatase Inhibitor Cocktail 3 (Sigma-Aldrich), 1% Protease Inhibitor Cocktail (Sigma-Aldrich), 400 U ml-1 RNasin (Promega). After 10 minutes incubation on ice, lysates were centrifuged 5 minutes at 13,000 rpm and the resulting supernatant was loaded onto 10-60% sucrose density gradients (100 mM KCl, 20 mM Hepes, 10 mM MgCl2). Gradients were then centrifuged in a SW40Ti rotor (Beckman Coulter) at 37,000 rpm for 150 minutes and polysomal fractions were monitored through a live OD254 nm measurement on a BioLogic LP System (BIO-RAD) followed by collection of 12 fractions. RNA from each of these fractions was extracted and distribution of particular mRNAs over the fractions was analyzed by qPCR.

Example 5: Translation Fidelity Assays

Programmed −1 ribosomal frameshifting (−1 PRF) assays Dual luciferase assays (Promega), and statistical calculations were performed as previously described (Grentzmann et al. (1998) *RNA* 4, 479-486; Harger and Dinman (2003) *RNA* 9, 1019-1024; Jacobs and Dinman (2004) *Nucleic acids Res.* 32, e160). Briefly, wild type and mutant Ba/F3 cells were mock-electroporated or electroporated with plasmids harbouring the in frame control, the out of frame control, or a −1 PRF signal from the human IL7R gene between the upstream renilla and downstream firefly luciferase open reading frames (FIG. 1) [Belew, A. T. et al. (2014) *Nature* 512, 265-269]. In the −1 PRF signal containing construct, the production of the firefly luciferase protein is dependent on a frameshifting event.

Three million cells were electroporated with 15 µg of each plasmid in 400 µl serum-free medium in 4 mm cuvettes using an exponential decay protocol (300V, 950 µF), and immediately transferred to 4 mL of pre-warmed recovery medium (10% FBS, IL3, sodium pyruvate and MEM non-essential amino acids). Twenty four hours later, cells were lysed in 100 µl lysis buffer, and luciferase readings were collected in 96 well half-area white plates (10 µl of lysate per read) on an EnSpire plate reader with two injectors (PerkinElmer). The percent frameshifting was determined by dividing the firely/renilla signal ratio in cells containing a −1 PRF construct or the out of frame control by the firefly/renilla signal ratio in the corresponding cells containing the in frame control construct.

Nonsense and Missense Suppression Assays

Nonsense suppression analysis is carried out in the same way as described above, except a STOP codon is introduced between the renilla and firefly luciferase genes. In such a construct, the production of the firefly luciferase protein is dependent on a STOP codon read-through event (FIG. 2).

Missense suppression is assayed by employing a construct containing the R218S single base substitution in the firefly luciferase active site. In such a construct, the activity of firefly luciferase is dependent on the incorporation of a near-cognate arginine instead of a cognate serine (FIG. 2).

Example 6: Proteasome Activity Assay

Proteasome activity is tested on Ba/F3 and Jurkat cells expressing RPL10 WT or R98S using Proteasome-Glo Chymotrypsin-Like, Trypsin-Like and Caspase-Like Cell-Based Assays (Promega) according to the manual included in the kit (FIG. 5).

Example 7: The RPL10 R98S Mutation Increases Translation Efficiency

To characterize the effects of RPL10 R98S on ribosome function, we first looked at cellular levels of newly synthesized proteins using an assay that measures incorporation of a labelled amino acid in all cellular proteins. These experiments indicated that Ba/F3 cells expressing RPL10 R98S produce 25% more de novo proteins when compared to RPL10 WT cells (FIG. 3A). In agreement with this, expression of the GFP reporter present in our RPL10 expression constructs was higher in the RPL10 R98S expressing cells (average MFI of 1358 in RPL10 WT cells versus 2154 in RPL10 R98S cells FIG. 3B, left). Similarly, Jurkat cells electroporated with a GFP reporter plasmid displayed an elevated GFP MFI upon RPL10 R98S expression (average MFI of 2174 in RPL10 WT cells versus 3764 in RPL10 R98S cells; FIG. 3B, right) This increase in detected proteins could be due to an upregulation in protein translation by the ribosome. In agreement with this, the mutant expressing Ba/F3 cells show downregulated phospho-eIF2α levels (FIG. 3C). Upregulation of translation efficiency was further supported by the fact that all analyzed transcripts shifted towards higher polysomal fractions in polysome profiling experiments on Ba/F3 cells, indicating a general increase in translation efficiency (FIG. 3D).

Example 8: RPL10 R98S Ba/F3 Cells Show Increased Translation Fidelity

In order to verify if the RPL10 R98S mutation influences translation fidelity by the ribosome, we performed dual luciferase reporter assays in which firefly activity depends on the fidelity of amino acid incorporation, reading of a STOP codon, or programmed −1 ribosomal frameshifting (see figures in methods section above). RPL10 R98S expressing cells showed a 70-80% reduction of normalized firefly activity in all three assays, indicating higher translation accuracy (FIG. 4).

Example 9: RPL10 R98S Cells Show Reduced Protein Degradation

In order to investigate whether the RPL10 R98S associated changes in ribosome function have implications on degradation of cellular proteins, the three major protease activities of the proteasome were analysed in RPL10 WT versus R98S cells. RPL10 R98S Ba/F3 cells displayed 28% and 23% decreases in chymotrypsin-like and caspase-like activity of the proteasome as compared to WT (FIG. 5, top). Similarly, RPL10 R98S expressing Jurkat cells had a 17% and 25% decrease in proteasomal chymotrypsin-like and caspase-like activity as compared to WT (FIG. 5, bottom).

Example 10: Hyperactive NOTCH1 Signalling Rescues RPL10 R98S Associated Cell Proliferation Defects without Affecting Translation Fidelity RPL10 WT and R98S expressing Ba/F3 cells were transduced with retroviral vectors harbouring MSCV plasmids encoding either the active cleaved form of Notch1 (intercellular Notch—ICN) (SEQ ID NO:5) followed by an IRES sequence and an mcherry reporter or mCherry alone. After sorting for mCherry, cells were plated at 100,000 cells/ml, and cell numbers were counted every 24 hours on a on a Guava Easycyte HT flow cytometer (Millipore). Translational fidelity in RPL10 WT and R98S cells harbouring the ICN-IRES-mCherry or mCherry constructs was assayed as described above.

Mutant RPL10 R98S Ba/F3 cells display a clear growth defect as compared to wild type cells during the exponential growth phase (FIG. 6A). The exogenous addition of NOTCH1-ICN did not have any effect on the growth rate of wild type cells, but it rescued the growth defect of mutant cells (FIG. 6A). However, while the growth defect of mutant cells was rescued with NOTCH1-ICN, their translational alterations and increased ribosomal accuracy remained (FIG. 6B).

Figure 21:
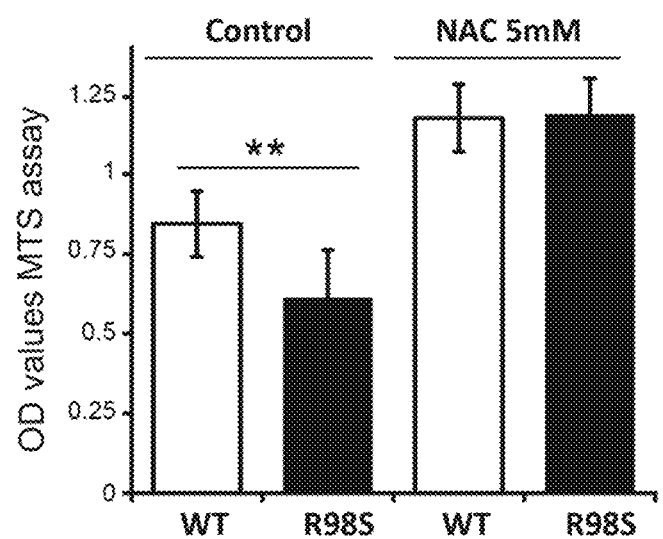
FIG. 21 shows a cell proliferation analysis of Ba/F3 RPL10 WT and R98S clones either untreated or treated with 5 mM N-acetyl-L-cysteine (NAC). Cell proliferation is quantified using the MTS proliferation assay, in which colorimetric formazan production is measured by optical densitometry. The bar-graphs represent average+/−st dev of measured optimal density (OD) of the colorimetric MTS assay.

Example 11: Treatment with N-Acetyl-L-Cysteïne (NAC) Rescues RPL10 R98S Associated Proliferation Defects RPL10 WT and R98S expressing Ba/F3 cells were plated at 0.25×10⁶ cells/ml and were grown for 48 hours under exponential growth conditions in the presence or absence of 5 mM N-acetyl-L-cysteine (NAC). The MTS cell proliferation assay in which colorimetric formazan production is measured by optical densitometry was used as read-out for cell numbers. R98S Ba/F3 cells displayed lower OD values indicating reduced cell numbers as compared to WT cells in the absence of NAC (due to the proliferation defect in exponential growth condition). These reduced cell numbers were entirely rescued by addition of 5 mM NAC (FIG. 21).

Examples 10 and 11 support that the growth defect associated with expression of an RPL10 mutation construct, can be rescued by expression of the NOTCH1-ICN allele or by addition of antioxidant agents such as NAC, suggesting that these manipulations will have a positive effect on protein expression.

Example 12: RPL10 R98S Conditional Knock-in Mouse Model

Figure 7:
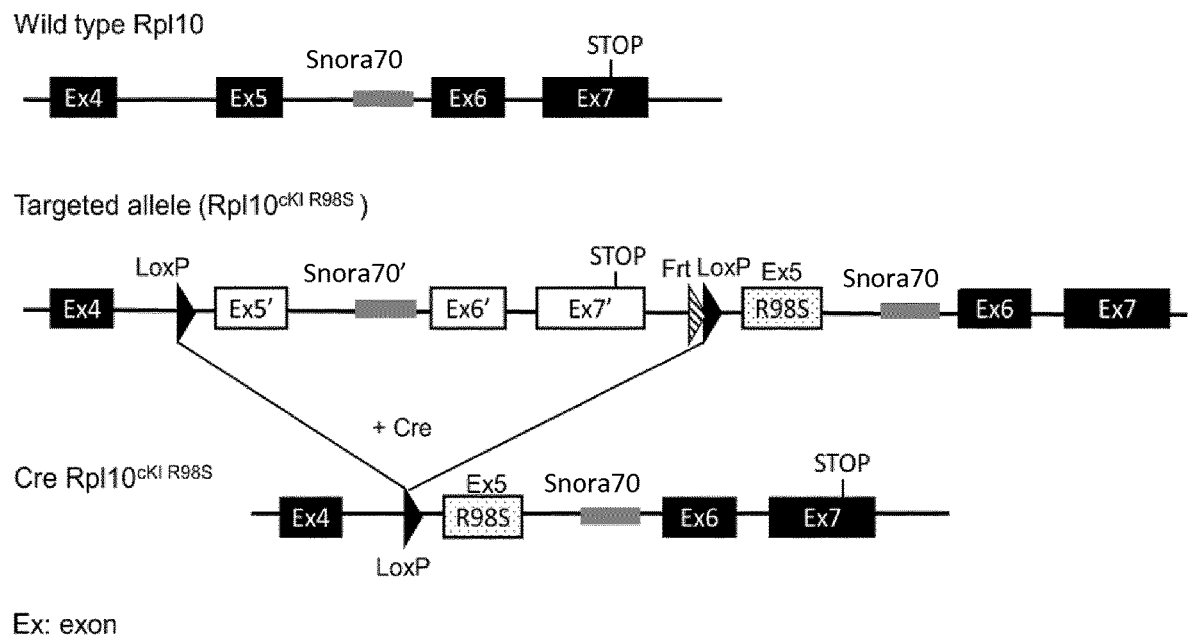
FIG. 7 shows a schematic representation of the conditional $Rpl10^{cKI\ R98S}$ mouse model FIG. 8. shows that RPL10 R98S expressing mouse hematopoietic cells display increased expression and phosphorylation of Jak-Stat signalling components. Representative immunoblots of expression and phosphorylation of Jak-Stat proteins in hematopoietic cells derived from Rpl10cKI R98S (labelled as WT in the figure) and MX-Cre Rpl10cKI R98S (labelled as R98S in the figure) mice.

Generation of a conditional Rpl10 R98S knock-in mouse line (RPL10cKI R98S) was performed by the company Polygene AG (Rumlang, Switzerland). In this model, the wild type genomic region of Rpl10 encompassing exons 5 up to 7 was flanked with loxP sites. Downstream of this cassette, a mutant version of exon 5 encoding the R98S mutation was placed (FIG. 7, targeted allele RPL10$^{cKI\ R98S}$). In this configuration, prior to Cre recombinase mediated recombination, the wild type gene containing its wild type introns including Snora70 are expressed. After Cre recombination, the genomic configuration is identical to wild type with the exception of a remaining loxP site, and the introduced R98S point mutation (FIG. 7, Cre RPL10$^{cKI\ R98S}$).

To generate the targeting vector, the homology arms from a C57Bl/6-derived BAC were subcloned, and a synthetic 1293 bp loxP-flanked cassette containing the Rpl10 genomic sequence encompassing exons 5-7 spiked with 3 silent changes was used. Upstream of the upstream loxP site, an FRT-flanked neomycin selection cassette was added for selection in cell culture. The homologous arms had sizes of 2.5 and 3.2 kbp. Targeting of C57Bl/6N-derived ES cells (PolyGene AG) yielded 8 out of 388 clones with correct configuration verified by PCR and Southern hybridization. Blastocyst microinjection of these clones into C57Bl/6grey-derived embryos (PolyGene AG) resulted in chimeric mice that transmitted to germ line after mating with C57Bl/6grey Flp deleter mice. Neo-less correct heterozygous F1 genotypes were verified by PCR. Rpl10 R98S conditional knock-in mice were crossed to MX-Cre C57Bl/6 mice (B6.Cg-Tg (Mx1-cre)1Cgn/J strain Jackson Laboratories). For the described experiments, lineage negative cells were isolated (EasySep Mouse Hematopoietic Progenitor Cell enrichment kit, Stemcell Technologies) from 6-8 weeks old male mice carrying the conditional Rpl10 R98S allele together with an MX-Cre allele (MX-Cre Rpl10$^{cKI\ R98S}$) and from conditional Rpl10 R98S controls (Rpl10$^{cKI\ R98S}$). Wells were plated at 2000 cells/ml in Methocult GF M3534 medium (Stemcell Technologies) containing 1250 units/ml of IFNβ (R&D systems) to induce recombination of the conditional RPL10 R98S allele. After 10-15 days, cells were collected and lysed in lysis buffer (Cell Signalling Technology) with addition of 5 mM Na$_3$VO$_4$ and protease inhibitors (Complete, Roche) and analyzed via immunoblotting. Expression of the R98S mutation upon Cre recombination was confirmed by Sanger sequencing of cDNA of the region encoding Rpl10 R98.

Figure 8:
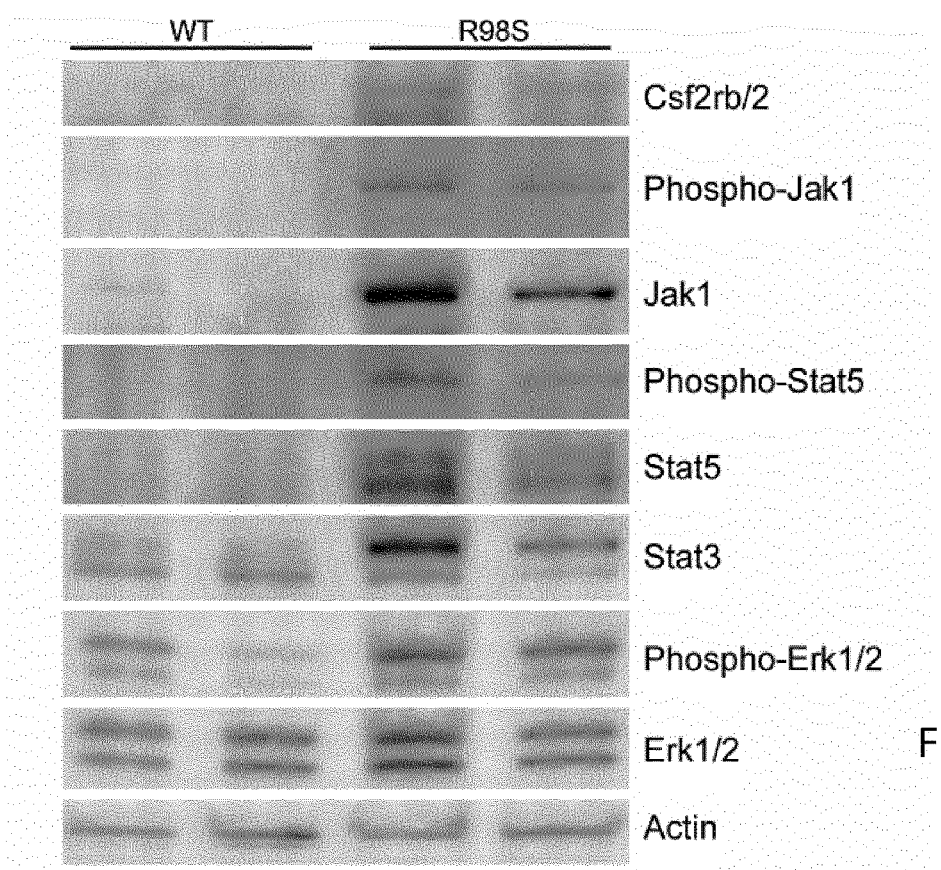

In mouse hematopoietic cells derived from a conditional Rpl10 R98S knock-in mouse model, elevated protein expression and/or phosphorylation was confirmed for Csf2rb/2, Jak1, Stat3, Stat5 and Erk in (FIG. 8).

Figure 20:
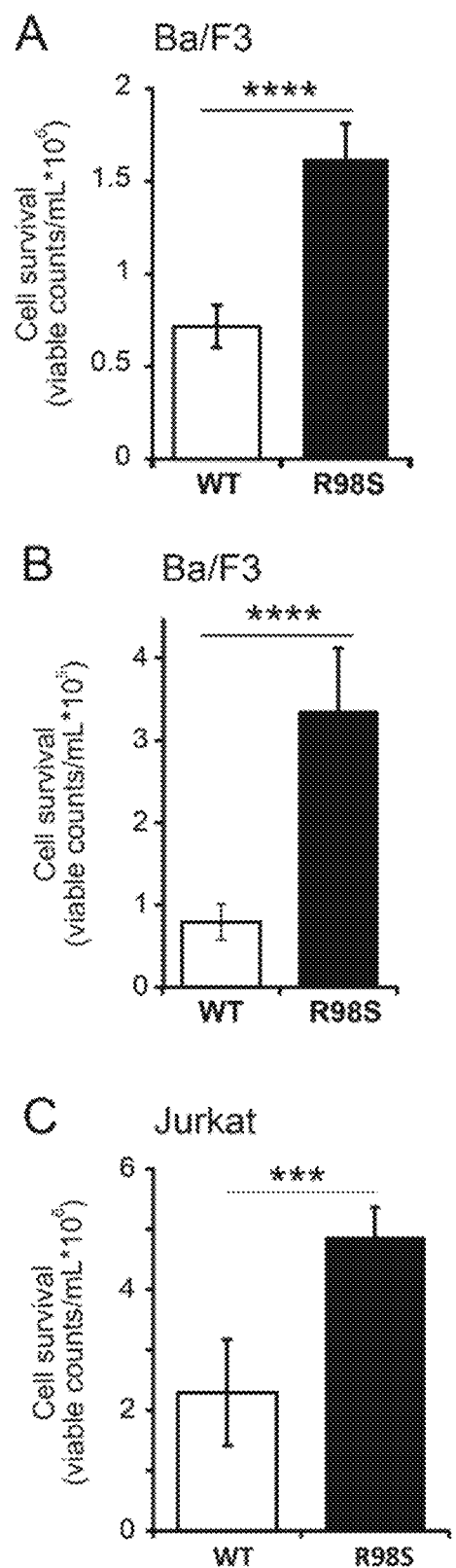
FIG. 20 illustrates that RPL10 R98S cells show enhanced survival under nutrient poor overgrowth conditions A) Viable cell counts of RPL10 R98S and WT expressing Ba/F3 cells that were cultured for 5 days without medium refreshment. In this overgrowth condition, Ba/F3 RPL10 R98S mutant cells displayed a survival benefit as compared to RPL10 WT cells. B) Ba/F3 clones were grown under normal conditions for 3 days, until their overgrowth condition started. At this moment, the culture media was replaced by media that had been exhausted by RPL10 WT Ba/F3 cells. After 2 days of culturing in the exhausted condition, the viable cell counts were determined comparing RPL10 WT clones versus R98S clones. C) Viable counts of RPL10 R98S and WT expressing JURKAT cells that were cultured for 5 days without medium refreshment. Averages+/−st dev are plotted.

Example 13: RPL10 R98S Cells Show Enhanced Survival Under Nutrient Poor Overgrowth Conditions RPL10 R98S and WT expressing Ba/F3 were cultured for 5 days without medium refreshment. In this overgrowth condition, Ba/F3 RPL10 R98S mutant cells displayed a survival benefit as compared to RPL10 WT cells (FIG. 20A). To ascertain that this survival benefit was independent of differences in residual nutrients due to the growth defect of RPL10 R98S cells in exponential phase (De Keersmaecker et al. (2013) cited above), the RPL10 WT and R98S Ba/F3 cells were cultured in nutrient deprived conditioned media from overgrown WT Ba/F3 cells, leading to an even stronger survival benefit for the RPL10 R98S cells (FIG. 20B).

Similarly, RPL10 R98S expressing Jurkat cells in overgrowth condition (no medium exchange for 5 days) displayed an enhanced survival over RPL10 WT expressing JURKAT cells (FIG. 20C).

The present example illustrates that cells with mutant RPL10 have an even better chance in survival under stress conditions. Use of cells with RPL10 mutations for protein expression is expected to give a higher protein yield, in view of the higher biomass that can be expected. It is expected that this advantage is even more pronounced under stress conditions such as the synthesis of proteins of an expression construct, which puts a significant metabolic burden on a cell.

Example 14: The T-Cell Leukaemia Associated Ribosomal RPL10 R98S Mutation Enhances JAK-STAT Signalling Quantitative Proteomics Cells derived from 3 monoclonal Ba/F3 cultures expressing WT or R98S RPL10 were lysed in lysis buffer (Cell Signalling Technology) with addition of 5 mM Na3VO4 and protease inhibitors (Complete, Roche). Twenty µg of protein as determined by the Bradford method were processed for quantitative proteomics as described in the supplementary methods. The entire list of identified proteins was ranked according to log 2 fold changes and used as input for GSEA against the MSigDB C2 KEGG gene sets [Subramanian A. & Tamayo P. (2005) *Proc Natl Acad Sci USA*. 103, 155545-155550; Mootha V K. et al. (2003) *Nat Genet*. 34, 267-273]. Only GSEA results with a FDR q-value <0.25 were considered.

Programmed −1 Ribosomal Frameshifting (−1 PRF) Assays

Dual luciferase assays (Promega), and statistical calculations were performed as follows. Briefly, Hek293T cells or Ba/F3 cells were transfected with plasmids harbouring the in frame control, the out of frame control, or a −1 PRF signal between the upstream renilla and downstream firefly luciferase open reading frames (FIG. 1). Further details on the assay are described in example 5.

Quantitative Proteomics

Cells derived from 3 monoclonal Ba/F3 cultures expressing either WT or R98S RPL10 were lysed in lysis buffer (Cell Signalling Technology) with addition of 5 mM Na3VO4 and protease inhibitors (Complete, Roche). Twenty μg of protein as determined by the Bradford method was run through a 12% SDS-PAGE (Bio-Rad) and Coomassie stained using Simply Blue Safe Stain (Invitrogen). Entire SDS-PAGE gel lanes were sliced into pieces and proteins were reduced-alkylated before overnight digestion using Trypsin/LysC Mix (Promega). The resulting peptides were extracted and vacuum dried. Peptides were desalted on C18 StageTips and each sample was fractionated using SCX StageTips. All fractions were again vacuum dried prior to mass spectrometric analysis. For LC MS/MS analysis, peptides were resuspended and separated by reversed-phase chromatography on a Dionex Ultimate 3000 RSLC nanoU-PLC system in-line connected with an Orbitrap Q Exactive Mass-Spectrometer (Thermo Fischer Scientific). Database searching was performed using Mascot 2.3 (Matrix Science), MS-Amanda and SEQUEST in Proteome Discoverer v.1.4 against a homemade database consisting of the human RL10 R98S protein (Uniprot Accession: P27635) and in the mouse reference proteome (UniProt release 2015_04; 45182 sequences). All searches were performed with trypsin cleavage specificity, up to 2 missed cleavages were allowed, and ion mass tolerance of 10 ppm for the precursor and 0.05 Da for the fragments. Carbamidomethylation was set as a fixed modification, whereas oxidation (M), acetylation (Protein N-term), phosphorylation (STY) were considered as variable modifications. Further processing of mass spectrometry data was performed in Scaffold 4 software (Proteome Software), using the quantitative value (normalized total spectra) setting. Unsupervised average-linkage hierarchical clustering was performed in IBM SPSS 23.0 with Euclidean distance as similarity metric. The entire list of identified proteins was ranked according to log 2 fold changes and used as input for GSEA against the MSigDB C2 KEGG gene sets.[1,2] Only GSEA results with a FDR q-value <0.25 were considered.

Polysomal and Total mRNA Sequencing

Up to three polysomal and total RNA sequencing libraries were generated for each of the 3 monoclonal Ba/F3 cultures expressing either WT or R98S RPL10. An amount of 15×106 cells were pelleted by centrifugation (5 min, 1500 rpm) and were lysed in ice-cold 100 mM KCl, 20 mM Hepes (Life technologies), 10 mM $MgCl_2$, 1 mM DTT, 1% sodium deoxycholate, 1% NP-40 (Tergitol solution, Sigma-Aldrich), 100 μg ml-1 cycloheximide, 1% Phosphatase Inhibitor Cocktail 2 (Sigma-Aldrich), 1% Phosphatase Inhibitor Cocktail 3 (Sigma-Aldrich), 1% Protease Inhibitor Cocktail (Sigma-Aldrich), 100 U ml-1 RNasin (Promega). After 10 minutes incubation on ice, lysates were centrifuged 5 minutes at 13,000 rpm and the resulting supernatant was loaded onto 10-60% sucrose density gradients (100 mM KCl, 20 mM Hepes, 10 mM MgCl2). Gradients were then centrifuged in a SW40Ti rotor (Beckman Coulter) at 37,000 rpm for 150 minutes and polysomal fractions were monitored through a live OD254 nm measurement on a BioLogic LP System (Bio-Rad). Polysomal fractions were collected on a fraction collector 2110 (Bio-Rad), followed by addition of proteinase K (50 μg/ml) and incubation for 30 min at 37° C. NaOAc 3M, pH5.5 (1/10 volume) was added followed by RNA extraction using the phenol/chloroform method with inclusion of an extra washing step with 70% ethanol. Next generation sequencing libraries were generated from total RNA and polysomal RNA using the TruSeq Stranded mRNA Sample Prep Kit (Illumina) and were sequenced on a NextSeq instrument (Illumina) using a 50-bp single read protocol. Ribosomal RNA and tRNA contamination were computationally removed and the remaining reads were aligned by Tophat v2.0.11 to the to the mm10 mouse reference genome (GRCm38) using the transcriptome defined by Mus_musculus.GRCm38.76.6 Only reads mapping uniquely and with high quality (mapqual>10) were retained for further analyses. Gene expression was estimated from exon-mapped reads, which were counted using HTSeq-count in union mode.

The DESeq2 R package[8] was applied on total RNA to identify significant differences in transcription between R98S and WT conditions (FDR<0.1). Translational efficiency (TE) was estimated, for each gene and within each condition, as the ratio between polysome-associated mRNA counts and total mRNA counts. Differences in TE between R98S and WT conditions were calculated as a TE(R98S)-to-TE(WT) ratio. The Babel R package[9] was used to estimate the statistical significance of detected TE differences between the R98S and WT condition. This method builds a regression model of polysome mRNA counts and total mRNA counts to identify genes whose polysome mRNA levels are not sufficiently explained by their total mRNA levels.

Results

Figure 9:
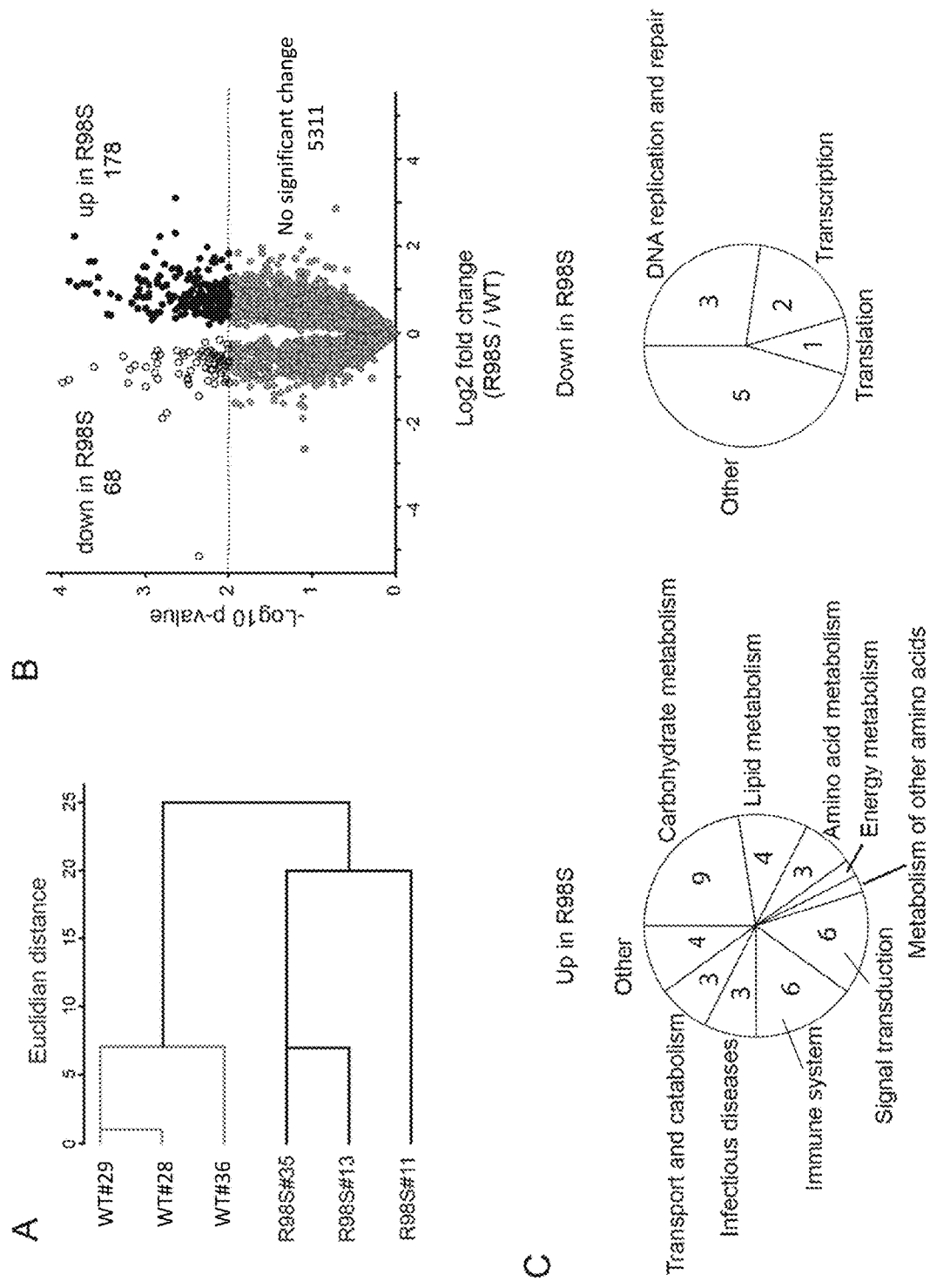
FIG. 9 shows a mass spectrometry screen for proteins and pathways showing differential expression between RPL10 WT and R98S cells. A) Hierarchical clustering analysis of the differential proteome results of the three analyzed RPL10 Wild type (WT #29, WT #36 and WT #28) and RPL10 R98S mutant (R98S #13, R98S #35 and R98S #11) cell clones. B) Volcano plot of the quantitative proteomics data comparing RPL10 WT and R98S samples. The dashed line illustrates the cut-off for significance (p<0.01; T-test). Red dots represent the 178 proteins that are significantly upregulated in the R98S samples, green dots correspond to the 68 proteins that are significantly downregulated. C) Pathways/processes that are significantly up- (left) or down- (right) regulated in R98S samples. The numbers in the pie chart represent the number of significant pathways corresponding to each process that are up or down in the cells.

Four Percent of Proteins Show Significantly Altered Expression Levels in RPL10 R98S Cells To gain insights into the mechanisms by which the RPL10 R98S mutation contributes to T-ALL development, we screened for proteins that are differentially expressed between RPL10 wild type (WT) and RPL10 R98S (R98S) expressing cells. These experiments were conducted in the mouse pro-B Ba/F3 cell line, a well-established hematopoietic model for oncogenic studies. A label-free quantitative proteomics approach was used to compare the abundance of the 5557 most highly expressed proteins, and unsupervised hierarchical clustering showed that WT and R98S samples grouped into 2 independent clusters (FIG. 9A). Whereas 96% (5311/5557) of proteins did not change significantly between WT and R98S samples, 3% (178) were significantly upregulated in the R98S samples, and 1% (68) were significantly downregulated (FIG. 9B). Gene Set Enrichment Analysis (GSEA) revealed that many of the overexpressed proteins in the R98S cells fit into pathways of cell metabolism, signalling, and function of the immune system. In contrast, proteins related to essential cellular processes such as DNA replication and repair, transcription and translation, were downregulated in the mutant cells (FIG. 9C). RPL10 R98S cells thus showed altered expression of 4% of proteins, with differential expression of several known cancer-associated processes.

RPL10 R98S Cells Express Elevated Levels of Jak-Stat Signalling Mediators

Figure 10:
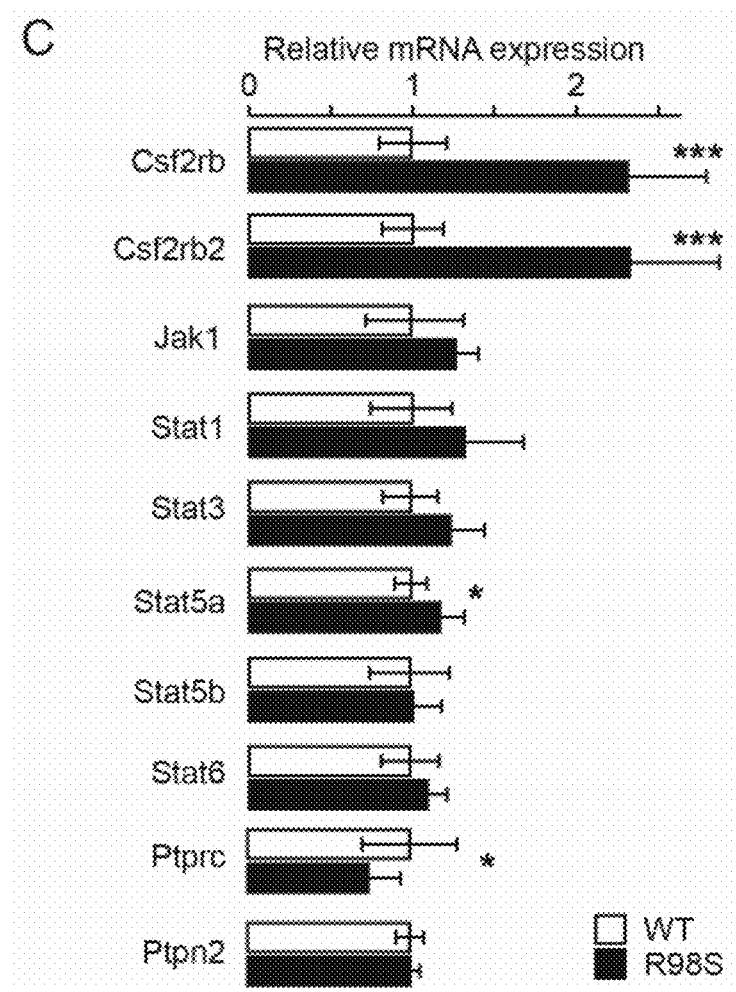
FIG. 10 illustrates that RPL10 R98S cells express altered levels of Jak-Stat signalling components. A) left: GSEA plot illustrating enrichment of JAK-STAT pathway proteins in the proteins upregulated in RPL10 R98S cells. FDR: false discovery rate. right: Volcano plot of the Jak-Stat signalling mediators identified by mass spectrometry. The dashed line illustrates the cut-off for significance (p<0.05; T-test). Red dots represent proteins that are significantly upregulated in the R98S samples, green dots correspond to proteins that are significantly downregulated in the R98S cells. B) Left: Immunoblot validation of differential expression of Jak-Stat pathway genes in three independent clones of RPL10 R98S versus WT expressing cells. The figure shows a representative blot of 3 independent experiments. Right: Quantification of the immunoblot validations. Signal of the JAK-STAT pathway proteins was normalized for loading. The quantification represents the average+/−standard deviation of a representative experiment comparing 3 independent RPL10 WT versus 3 independent R98S cell clones. P-values were calculated using a T-test. C) Quantification of JAK-STAT mRNA levels in RPL10 WT versus R98S expressing Ba/F3 cells. Results were obtained by mRNA sequencing on 3 RPL10 WT versus R98S Ba/F3 clones. The represented RNA levels are DESeq2-normalized counts relative to the WT. Significant changes (FDR<0.1) in RNA levels between R98S and WT were estimated using the DESeq R package. *p<0.05, p<0.01, *p<0.01.

Analysis of the GSEA results of the proteomic data revealed an enrichment of JAK-STAT pathway members among the upregulated proteins in the RPL10 R98S cells (FIG. 10A, left). Because of the importance of the JAK-STAT pathway in T-ALL pathogenesis and cancer in general, these results prompted a more detailed investigation. Three Jak kinases (Jak1, Jak3 and Tyk2) were detected in the mass spectrometry screen, of which Jak1 showed a significant 1.9-fold upregulation in the R98S cells (FIG. 10A, right). Of the five Stat proteins that were detectable, only Stat2 was unchanged. All others trended towards upregulation in the R98S cells, with Stat6 attaining a statistically significant increase. The mass spectrometric data also revealed a significant 2- to 3-fold upregulation of the Csf2rb and Csf2rb2 proteins. Csf2rb corresponds to the common beta chain of the receptor for IL3, IL5 and GM-CSF, whereas Csf2rb2 is an IL3-receptor specific beta subunit in mouse [Hara T, Miyajima A. (1992) *EMBO J.* 11, 1875-1884]. IL3, IL5 and GM-CSF signalling are all mediated via JAK-STATs. JAK-STAT signalling is tightly controlled via negative regulators including Pias proteins, Socs proteins and phosphatases such as Ptprc and Ptpn2 [Van Vlierberghe P. (2012) *J Clin Invest.* 122, 3398-3406]. Only Ptprc and Ptpn2 were detectable among the mass spectrometry data, and Ptprc was significantly downregulated in the R98S cells (FIG. 10A, right). Immunoblot analysis of Jak-Stat cascade proteins confirmed upregulation of Csf2rb and Csf2rb2, Jak1, Stat1, Stat3, Stat5a, Stat5b, Stat6, downregulation of Ptprc and no change for Ptpn2 in R98S cells (FIG. 10B). As no consistent changes were detected for Tyk2 and Jak3 by immunoblot, these were not considered in further analyses. Whereas the protein changes detected for Csf2rb/2, Stat5a and Ptprc were associated with corresponding changes on mRNA level, the transcripts of the other genes were unchanged in R98S cells (FIG. 10C).

Figure 11:
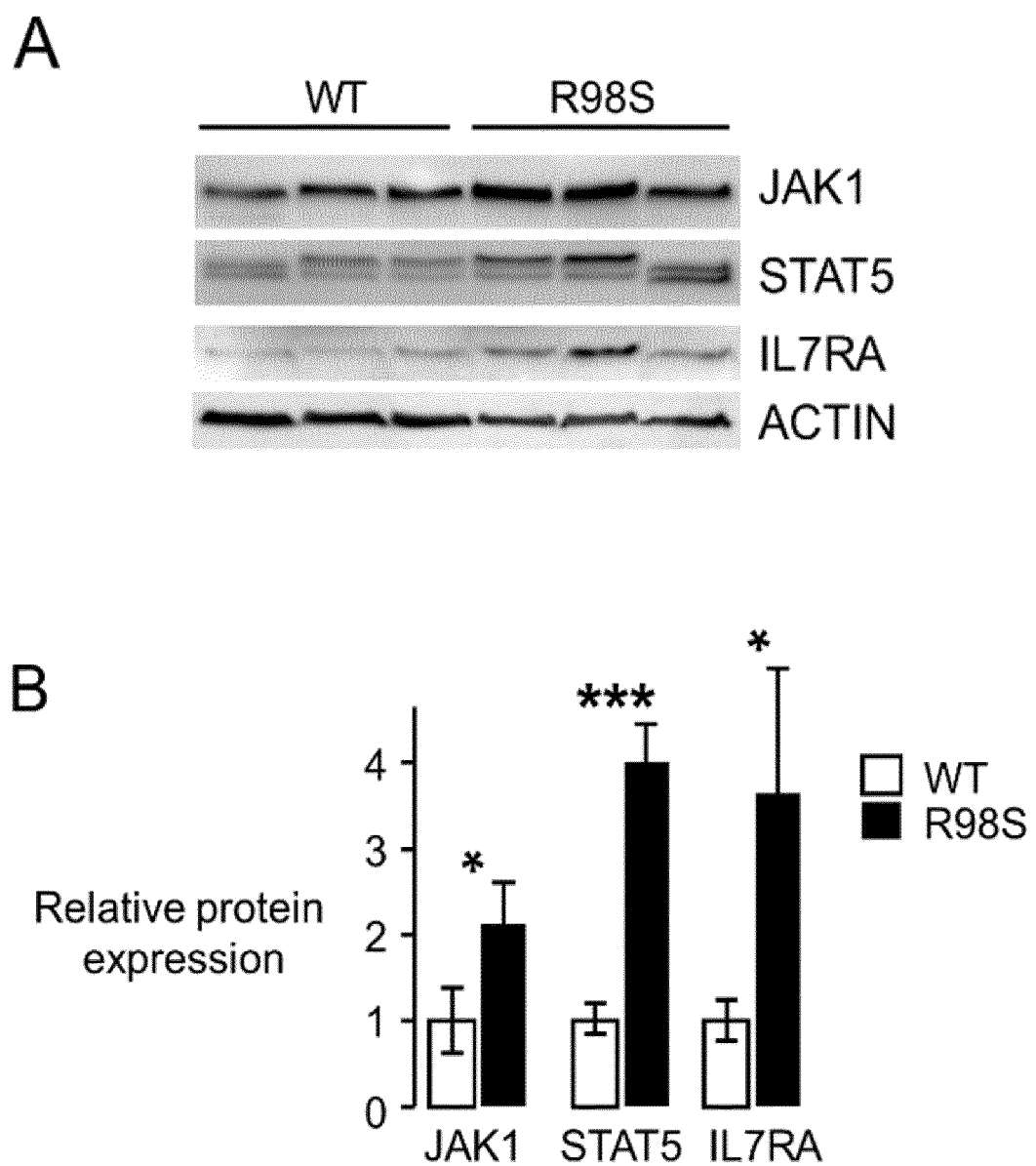
FIG. 11 shows that RPL10 R98S T-ALL patient samples have elevated expression of the JAK-STAT cascade, A) Immunoblot analysis of JAK-STAT pathway protein expression in 3 RPL10 WT and 3 RPL10 R98S mutant human T-ALL xenograft samples. Only those components of the JAK-STAT pathway for which significant changes were observed are represented. B) Quantification of the immunoblots shown in panel (A). The bars indicate the average+/−standard deviation of 3 independent RPL10 WT T-ALL patient samples versus 3 RPL10 R98S positive patient samples. P-values were calculated using a T-test. *p<0.05, **p<0.01.

RPL10 R98S T-ALL Patient Samples have Elevated Expression of the JAK-STAT Cascade Immunoblotting of protein lysates from xenografted T-ALL patient samples confirmed elevated expression of JAK1 (2.1-fold) and STAT5 (4-fold) (FIG. 13A-B) in RPL10 R98S mutant T-ALL samples. None of these patient samples contained any IL7R-JAK-STAT mutations. The IL3 receptor is not expressed in T-ALL samples. Instead, the IL7 receptor is important for normal T-cell development and in T-ALL [Ribeiro D et al (2012). Adv. Boil. Reg. 53, 211-222]. Expression of the IL7RA chain was 3.7-fold upregulated in the RPL10 R98S T-ALL samples compared to RPL10 WT samples (FIG. 11A-B).

RPL10 R98S Decreases Programmed −1 Ribosomal Frameshifting on Several JAK-STAT Pathway mRNAs.

Figure 15:
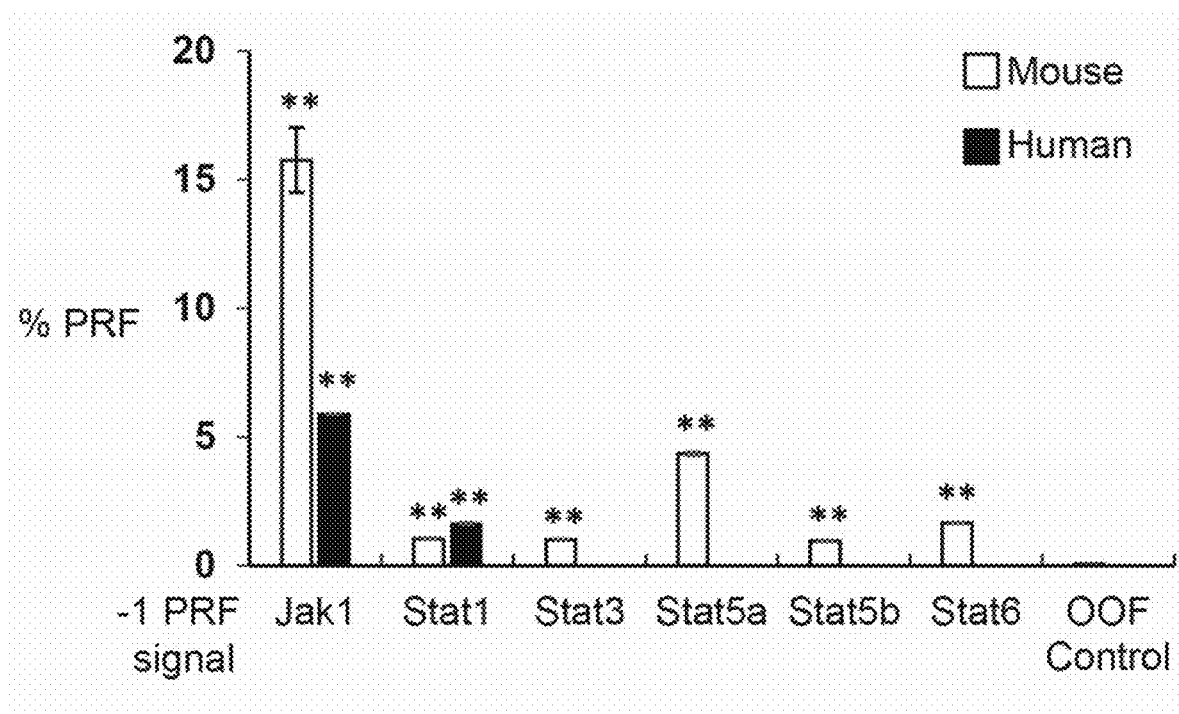
FIG. 15. Validation of −1 PRF signals by dual luciferase assays. Results from dual luciferase reporter assays in Hek293T cells testing −1 PRF levels on the indicated mouse and human PRF signals. Error bars denote standard errors. **p<0.01 compared to the out of frame (OOF) control (T-test).

We next investigated cellular mechanisms that could be contributing to the specific JAK-STAT overexpression. In this process, cis-acting mRNA elements (−1 PRF signals) direct translating ribosomes to slip on an mRNA by one base in the 5' direction, thus establishing a new reading frame. In mammalian cells, such −1 PRF events direct translating ribosomes towards premature termination codons, resulting in destabilization of the −1 PRF signal-containing mRNA (Klare N. et al. (2007) *J Mol Biol.* 373, 1-10; Advani V M & Dinman J D (2015) *Bioessays.* 38, 21-26). −1 PRF thus serves as a mechanism to fine-tune gene expression, and in silico algorithms predict that approximately 10% of human genes contain −1 PRF signals (Belew et al. (2014) cited above; Advani et al. (cited above). We have recently shown that several cytokine receptors, including the IL7RA chain, contain functional −1 PRF signals (Belew et al. (2014) cited above). To test whether the RPL10 R98S associated differences in JAK-STAT protein expression might be influenced by alterations in −1 PRF rates, the JAK-STAT pathway was first screened in silico for predicted −1 PRF signals. Enrichment analysis revealed that, within the 10% of human genes predicted to contain −1 PRF signals, the JAK-STAT pathway was enriched for such predicted signals using both GO (p=0.00056) and KEGG (p=0.0031) databases. Specifically, 30% of genes in the JAK-STAT pathway are predicted to contain −1 PRF signals compared to the 14.8% average in other pathways (FIG. 12A). Several human and mouse JAK-STAT pathway members for which RPL10 R98S associated differential protein levels were observed harbored such predicted −1 PRF signals. We validated the frameshifting-promoting activity of these signals using dual luciferase reporter constructs (FIG. 1) [Jacobs & Dinman et al. (2004) cited above]. Efficient rates of −1 PRF promoted by several mouse and human sequences were confirmed in human Hek293T cells (FIG. 15), as well as in mouse Ba/F3 cells (FIG. 12B-C). Interestingly, frameshifting levels induced by the signals in the mouse Stat genes were three to six times reduced in R98S cells (FIG. 12B). In contrast, high levels (15%) of frameshifting induced by the mouse Jak1 −1 PRF signal were unaffected by the R98S mutation in the Ba/F3 cells (FIG. 12B). A 1.5-fold and 2-fold decrease in frameshifting rates induced by human −1 PRF signals in IL7RA and JAK1 mRNAs were observed in cells expressing the R98S mutation (FIG. 12C). In summary, we have identified functional −1 PRF signals in several mouse and human JAK-STAT genes, the frameshifting levels on some of which were influenced by the RPL10 R98S mutation.

RPL10 R98S Cells Show Altered Proteasome Activity

Figure 13:
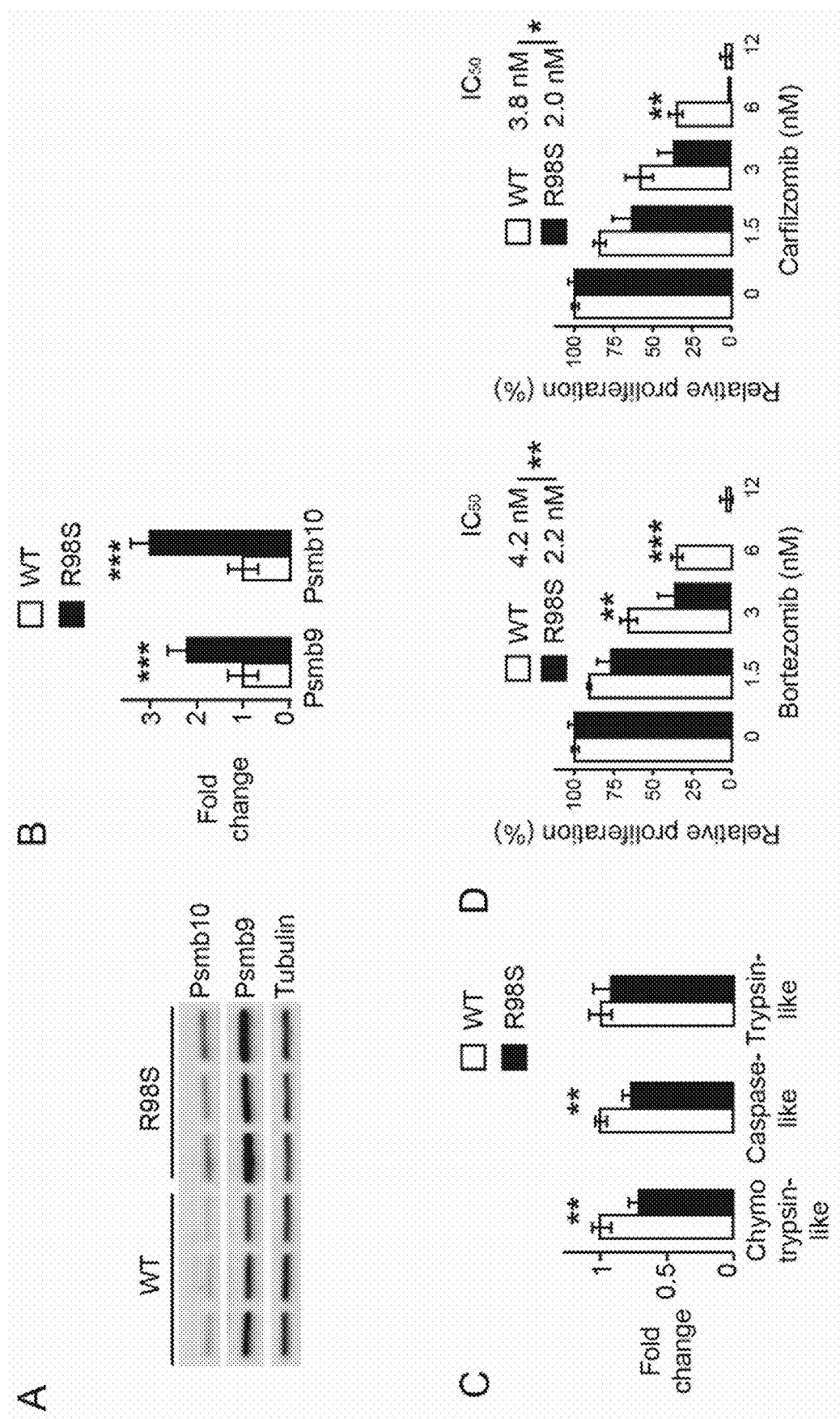
FIG. 13 illustrates that RPL10 R98S expressing cells show altered proteasome expression and activity and enhanced stability of Jak1. A) Immunoblot analysis of Psmb9 and Psmb10 expression in three independent clones of RPL10 R98S versus WT expressing cells. B) Quantification of the immunoblot validations shown in panel (A) C) Chymotrypsin-like, caspase-like and trypsin-like proteasomal activity of Ba/F3 cells expressing either WT or R98S RPL10. Plots show the average+/−standard deviation of three independent experiments comparing 3 biologically independent RPL10 WT versus 3 independent R98S cell clones. D) Relative proliferation of RPL10 WT and R98S cells treated with the indicated proteasome inhibitors measured using the ATPlite luminescence assay (Perking Elmer). The panel shows the average+/−standard deviation of a representative experiment comparing 3 biologically independent RPL10 WT versus 3 independent R98S cell clones. E) Immunoblots illustrating stability of Jak1 and Csf2rb/2 proteins as assessed by cycloheximide chase assays. F) Quantification of the immunoblots shown in panel (E). CHX: cycloheximide. The quantification represents the average+/−standard deviation of three independent experiments comparing 3 biologically independent RPL10 WT versus 3 independent R98S cell clones. P-values were calculated using a T-test *p<0.05, p<0.01, *p<0.001.
Figure 18:
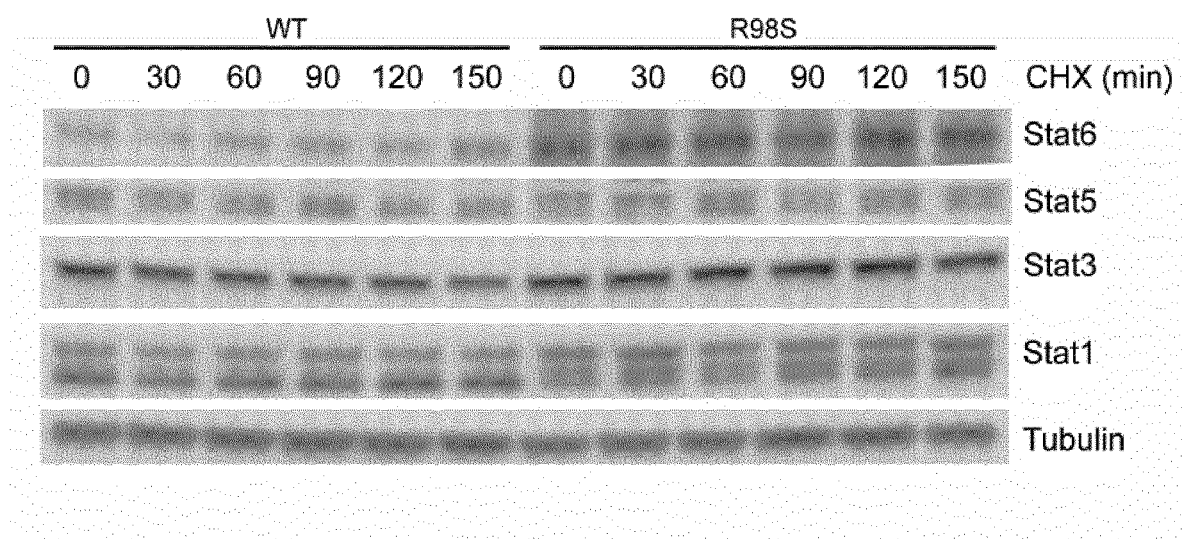
FIG. 18 shows that the stability of Stat proteins remained unchanged within 150 minutes of CHX-chase. Immunoblots illustrating protein stability as assessed by cycloheximide (CHX) chase assays.

Altered frameshifting rates can only partially explain the upregulation of the Jak-Stat cascade, as there was one −1 PRF signal (Jak1) in which frameshifting levels were unaffected by RPL10 R98S, despite a change at the protein level. Additionally, our computational tools could not identify −1 PRF signals in the mRNAs encoding some of the other proteins in which changes at the protein level were observed. The altered levels of mouse Stat proteins are also likely not entirely explained by altered −1 PRF alone. The transcriptional changes detected for Csfr2b/2, Stat5a and Ptprc (FIG. 10C) might partially explain the detected protein changes, and we investigated additional potential regulation at the translational or post-translational level. Polysomal RNA-seq analysis in the Ba/F3 cell model did not reveal any significantly altered translation efficiency of Csf2rb/2, Jak or Stat mRNAs (not shown). Interestingly, the mass spectrometry data revealed up- and downregulation of several proteasomal proteins in R98S cells (p<0.05), including upregulation of Psmb10, a catalytic subunit specific for the immunoproteasome (not shown). Upregulation of Psmb10 and Psmb9, another immunoproteasome specific catalytic subunit, was confirmed on immunoblots from both available mouse hematopoietic cell models (FIG. 13A-B and FIG. 16). In light of this, proteasome activities were assayed. R98S Ba/F3 cells displayed 28% and 23% decreases in chymotrypsin-like and caspase-like activity of the proteasome (FIG. 13C). Consistent with these observations, R98S cells were more sensitive to the proteasome inhibitors bortezomib, carfilzomib and MLN9708 (FIG. 13D). Interestingly, this altered proteasomal activity was not accompanied by differences in total protein polyubiquitination (FIG. 17). However, chase experiments after treatment with the translational inhibitor cycloheximide revealed increased stability of Jak1, but not Csf2rb/2, in R98S cells (FIG. 13E-F). Stat protein stability remained unchanged within the 150 minutes of the CHX-chase (FIG. 18). Altogether, our data indicate that RPL10 R98S cells display alterations in proteasome composition and activity, which may explain the increased stability of particular proteins such as Jak1 in these cells.

Discussion

We explored the molecular mechanism by which the RPL10 R98S mutation may drive selective upregulation of the JAK-STAT cascade. These effects may, at least partially, be mediated via reduced levels of −1 PRF on several JAK-STAT mRNAs. Initially described in viruses, it is becoming clear that this process is also relevant in mammalian cells (Belew et al. (2014) cited above). Only a limited set of predicted mammalian −1 PRF signals have been experimentally validated, including signals in several cytokine receptors such as IL7RA (Belew et al. (2014) cited above). We show the functionality of several additional predicted −1 PRF signals in mammalian cells, and that the JAK-STAT signalling cascade, downstream of cytokine receptors, is enriched for such signals. Levels of −1 PRF can be regulated by trans-acting proteins and miRNAs (Belew et al. (2014) cited above; Anzalone A V. et al. (2016) *Nat Methods*. 13, 453-458; Li Y. et al. (2014) *Proc Natl Acad Sci USA*. 111, E2172.) It is plausible that these −1 PRF signals function in fine-tuning and controlling immune responses, opening the possibility for oncogenic factors such as RPL10 R98S to deregulate this control mechanism. Given the relatively low rates of −1 PRF promoted by Jak-Stat signals, it is clear that the altered frameshifting levels detected here cannot fully explain the changes observed at the protein level, suggesting contribution by additional mechanisms. We propose a model in which R98S associated decreases in −1 PRF levels, combined with changes in the degradation of particular proteins and potential other mechanisms such as transcriptional regulation, leads to an oncogenic program. The specificity of the frameshifting alterations can be explained by the presence of unique −1 PRF signals in Jak-Stat genes. However, the specificity of the transcriptional and degradation phenotype is less clear. We show altered levels of specific catalytic components of the immunoproteasome. This finding, together with the altered proteasome activity in R98S cells, may indicate expression of a distinct type of proteasome, and is consistent with previously described 'mixed type' proteasomes containing constitutive as well as immuno-subunits [Klare N. et al. (2007) *J Mol Biol*. 373, 1-10; Dahlmann B. et al. (2002) J Mol Biol. 303, 643-653]. Different proteasome varieties show quantitative differences in cleavage efficiency of particular epitopes, which might provide a certain degree of protein specificity [Mishto M. et al. (2014) *Eur J Immunol*. 44, 3508-3521; Huber E M. et al. (2012) Cell. 148, 727-738]. Moreover, the proteomics screen revealed several proteins with E3 ubiquitin ligase activity to be differentially expressed between RPL10 WT and R98S cells (not shown), which may further account for the specificity of the observed degradation phenotype.

SEQUENCES DEPICTED IN THE APPLICATION

```
Human RPL10 cDNA sequence (SEQ ID NO: 1) and protein sequence (SEQ
ID NO: 2)
atgggccgccgccccgcccgttgttaccggtattgtaagaacaagccgtacccaaagtct
 M   G   R   R   P   A   R   C   Y   R   Y   C   K   N   K   P   Y   P   K   S cgcttctgccgaggtgtccctgatgccaagattcgcattttgacctggggcggaaaaag
 R   F   C   R   G   V   P   D   A   K   I   R   I   F   D   L   G   R   K   K gcaaaagtggatgagtttccgctttgtggccacatggtgtcagatgaatatgagcagctg
 A   K   V   D   E   F   P   L   C   G   H   M   V   S   D   E   Y   E   Q   L tcctctgaagccctggaggctgcccgaatttgtgccaataagtacatggtaaaaagttgt
 S   S   E   A   L   E   A   A   R   I   C   A   N   K   Y   M   V   K   S   C ggcaaagatggcttccatatccgggtgcggctccacccttccacgtcatccgcatcaac
 G   K   D   G   F   H   I   R   V   R   L   H   P   F   H   V   I   R   I   N aagatgttgtcctgtgctggggctgacaggctccaaacaggcatgcgaggtgcctttgga
 K   M   L   S   C   A   G   A   D   R   L   Q   T   G   M   R   G   A   F   G aagcccagggcactgtggccagggttcacattggccaagttatcatgtccatccgcacc
 K   P   Q   G   T   V   A   R   V   H   I   G   Q   V   I   M   S   I   R   T aagctgcagaacaaggagcatgtgattgaggccctgcgcagggccaagttcaagtttcct
 K   L   Q   N   K   E   H   V   I   E   A   L   R   R   A   K   F   K   F   P ggccgccagaagatccacatctcaaagaagtgggcttcaccaagttcaatgctgatgaa
 G   R   Q   K   I   H   I   S   K   K   W   G   F   T   K   F   N   A   D   E tttgaagacatggtggctgaaaagcggctcatcccagatggctgtggggtcaagtacatc
 F   E   D   M   V   A   E   K   R   L   I   P   D   G   C   G   V   K   Y   I cccagtcgtggccctctggacaagtggcgggccctgcactcatga
 P   S   R   G   P   L   D   K   W   R   A   L   H   S Mouse RPL10 (SEQ ID NO: 3)
MGRRPARCYR YCKNKPYPKS RFCRGVPDAK IRIFDLGRKK AKVDEFPLCG    50

HMVSDEYEQL SSEALEAARI CANKYMVKSC GKDGFHIRVR LHPFHVIRIN   100

KMLSCAGADR LQTGMRGAFG KPQGTVARVH IGQVIMSIRT KLQNKEHVIE   150

ALRRAKFKFP GRQKIHISKK WGFTKFNADE FEDMVAEKRL IPDGCGVKYI   200

PNRGPLDKWA LHS                                           213

Yeast RPL10 (SEQ ID NO: 4)
MARRPARCYR YQKNKPYPKS RYNRAVPDSK IRIYDLGKKK ATVDEFPLCV    50

HLVSNELEQL SSEALEAARI CANKYMTTVS GRDAFHLRVR VHPFHVLRIN   100
```

| | | | | |
|---|---|---|---|---|
| KMLSCAGADR | LQQGMRGAWG | KP<u>H</u>GLAARVD | IGQIIFSVRT | KDSNKDVVVE 150 |
| GLRRARYKFP | GQQKIILSKK | WGFTNLDRPE | YLKKREAGEV | KDDGAFVKFL 200 |
| SKKGSLENNI | REFPEYFAAQ | A | | 221 |

NOTCH1-ICN (SEQ ID NO: 5)
```
atgccgccgc tcctggcgcc cctgctctgc ctggcgctgc tgcccgcgct cgccgcacga
ggcccgcgag gatccatcgt ctacctggag attgacaacc ggcagtgtgt gcaggcctcc
tcgcagtgct tccagagtgc caccgacgtg gccgcattcc tgggagcgct cgcctcgctg
ggcagcctca acatccccta caagatcgag gccgtgcaga gtgagaccgt ggagccgccc
ccgccggccc agctgcactt catgtacgtg gcgcaggccg tggagccgcc cccgccgggc
cagctgcact tcatgtacgt ggcggcggcc gcctttgtgc ttctgttctt cgtgggctgc
ggggtgctgc tgtcccgcaa gcgccggcgg cagcatggcc agctctggtt ccctgagggc
ttcaaagtgt ctgaggccag caagaagaag cggcgggagc cctcgggcga ggactccgtg
ggcctcaagc ccctgaagaa cgcttcagac ggtgccctca tggacgacaa ccagaatgag
tgggggacg aggacctgga gaccaagaag ttccggttcg aggagcccgt ggttctgcct
gacctggacg accagacaga ccaccggcag tggactcagc agcacctgga tgccgctgac
ctgcgcatgt ctgccatggc ccccacaccg cccagggtg aggttgacgc cgactgcatg
gacgtcaatg tccgcgggcc tgatggcttc acccccgctca tgatcgcctc ctgcagcggg
ggcggcctgg agacgggcaa cagcgaggaa gaggaggacg cgccggccgt catctccgac
ttcatctacc agggcgccag cctgcacaac cagacagacc gcacgggcga gaccgccttg
cacctggccg cccgctactc acgctctgat gccgccaagc gcctgctgga ggccagcgca
gatgccaaca tccaggacaa catgggccgc accccgctgc atgcggctgt gtctgccgac
gcacaaggtg tcttccagat cctgatccgg aaccgagcca cagacctgga tgcccgcatg
catgatggca cgacgccact gatcctggct gcccgcctgg ccgtggaggg catgctggag
gacctcatca actcacacgc cgacgtcaac gccgtagatg acctgggcaa gtccgccctg
cactgggccg ccgccgtgaa caatgtggat gccgcagttg tgctcctgaa gaacggggct
aacaaagata tgcagaacaa cagggaggag acacccctgt ttctggccgc ccgggagggc
agctacgaga ccgccaaggt gctgctggac cactttgcca accgggacat cacggatcat
atggaccgcc tgccgcgcga catcgcacag gagcgcatgc atcacgacat cgtgaggctg
ctggacgagt acaacctggt gcgcagcccg cagctgcacg gagcccgct ggggggcacg
cccaccctgt cgcccccgct ctgctcgccc aacggctacc tgggcagcct caagcccgtcc
gtgcagggca agaaggtccg caagcccagc agcaaaggcc tggcctgtgg aagcaaggag
gccaaggacc tcaaggcacg gaggaagaag tcccaggacg gcaagggctg cctgctggac
agctccggca tgctctcgcc cgtggactcc ctggagtcac cccatggcta cctgtcagac
gtggcctcgc cgcactgct gccctcccg ttccagcagt ctccgtccgt gccctcaac
cacctgcctg ggatgcccga cacccacctg gcatcgggc acctgaacgt ggcggccaag
cccgagatgg cggcgctggg tggggcggc cggctggcct tgagactgg cccacctcgt
ctctcccacc tgcctgtggc ctctggcacc agcaccgtcc tgggctccag cagcggaggg
gccctgaatt tcactgtggg cggtgtccacc agtttgaatg gtcaatgcga gtggctgtcc
cggctgcaga gcggcatggt gccgaaccaa tacaaccctc tgcggggga gtgtggcacca
ggccccctga gcacacaggc cccctccctg cagcatggca tggtaggccc gctgcacagt
agccttgctg ccagcgccct gtcccagatg atgagctacc agggcctgcc cagcacccgg
ctggccaccc agcctcacct ggtgcagacc acgcaggtgc agccacaaaa cttacagatg
cagcagcaga acctgcagcc agcaaacatc cagcagcagc aaagcctgca gccgccacca
ccaccaccac agccgcacct ggcgtgagc tcagcagcca gcggcacct gggcggagc
ttcctgagtg gagagccgag ccaggcagac gtgcagccac tgggcccag cagcctggcg
gtgcacacta ttctgcccca ggagagcccc gccctgccca cgtcgctgcc atcctcgctg
gtcccacccg tgaccgcagc ccagttcctg acgccccct cgcagcacag stactcctyg
cctgtggaca acaccccag ccaccagcta caggtgcctg agcaccctt cctcaccccg
tcccctgagt ccctgacca gtggtccagc tgtccccgc attccaacgt ctccgactgg
tccgagggcg tctccagccc tcccaccagc atgcagtccc agatcgcccg cattccggag
gccttcaagt aa
```

NOTCH1-ICN (SEQ ID NO: 6)
[embodiment of SEQ ID NO: 6 wherein wherein AA2 is Pro, AA857 is Leu, AA860 is Ser and AA 891 is Ser]

| | | | | |
|---|---|---|---|---|
| <u>MPPLLAPLLC</u> | <u>LALLPALAAR</u> | <u>GPRGSIVYLE</u> | <u>IDNRQCVQAS</u> | <u>SQCFQSATDV</u> 50 |
| <u>AAFLGALASL</u> | <u>GSLNIPYKIE</u> | <u>AVQSETVEPP</u> | <u>PPAQLHFMYV</u> | <u>AQAVEPPPPA</u> 100 |
| <u>QLHFMYVAAA</u> | <u>AFVLLFFVGC</u> | <u>GVLLSRKRRR</u> | <u>QHGQLWFPEG</u> | <u>FKVSEASKKK</u> 150 |
| <u>RREPLGEDSV</u> | <u>GLKPLKNASD</u> | <u>GALMDDNQNE</u> | <u>WGDEDLETKK</u> | <u>FRFEEPVVLP</u> 200 |
| <u>DLDDQTDHRQ</u> | <u>WTQQHLDAAD</u> | <u>LRMSAMAPTP</u> | <u>PQGEVDADCM</u> | <u>DVNVRGPDGF</u> 250 |
| <u>TPLMIASCSG</u> | <u>GGLETGNSEE</u> | <u>EEDAPAVISD</u> | <u>FIYQGASLHN</u> | <u>QTDRTGETAL</u> 300 |
| <u>HLAARYSRSD</u> | <u>AAKRLLEASA</u> | <u>DANIQDNMGR</u> | <u>TPLHAAVSAD</u> | <u>AQGVFQILIR</u> 350 |
| <u>NRATDLDARM</u> | <u>HDGTTPLILA</u> | <u>ARLAVEGMLE</u> | <u>DLINSHADVN</u> | <u>AVDDLGKSAL</u> 400 |
| <u>HWAAAVNNVD</u> | <u>AAVVLLKNGA</u> | <u>NKDMQNNREE</u> | <u>TPLFLAAREG</u> | <u>SYETAKVLLD</u> 450 |
| <u>HFANRDITDH</u> | <u>MDRLPRDIAQ</u> | <u>ERMHHDIVRL</u> | <u>LDEYNLVRSP</u> | <u>QLHGAPLGGT</u> 500 |

| SEQUENCES DEPICTED IN THE APPLICATION |
|---|
| PTLSPPLCSP NGYLGSLKPG VQGKKVRKPS SKGLACGSKE AKDLKARRKK 550 |
| SQDGKGCLLD SSGMLSPVDS LESPHGYLSD VASPPLLPSP FQQSPSVPLN 600 |
| HLPGMPDTHL GIGHLNVAAK PEMAALGGGG RLAFETGPPR LSHLPVASGT 650 |
| STVLGSSSGG ALNFTVGGST SLNGQCEWLS RLQSGMVPNQ YNPLRGSVAP 700 |
| GPLSTQAPSL QHGMVGPLHS SLAASALSQM MSYQGLPSTR LATQPHLVQT 750 |
| QQVQPQNLQM QQQNLQPANI QQQQSLQPPP PPPQPHLGVS SAASGHLGRS 800 |
| FLSGEPSQAD VQPLGPSSLA VHTILPQESP ALPTSLPSSL VPPVTAAQFL 850 |
| TPPSQHSYSS PVDNTPSHQL QVPEHPFLTP SPESPDQWSS SSPHSNVSDW 900 |
| SEGVSSPPTS MQSQIARIPE AFK 923 | shRNA construct targeting mouse rpl10 (SEQ ID NO: 7)
5'-aaccgacgatcctattgtcatc-3' gRNA targeting RPL10 (SEQ ID NO: 8)
5'-tcttgttgatgcggatgacg-3'

RPL10 R98S donor oligo sequence(SEQ ID NO: 9)
5'-ctgtcagccc cagcacagga caacatcttg ttaatgctga tcacgtgaaa ggggtggagc cgcacccgga tatggaagcc atctttgcca caacttttta ccatgtactt attggcacaa attcgggca-3'

PCR primers for distinguishing RPL10 WT and R98S in Jurkat cells
Fw_WT:
5'-cttccacgtcatccgcatc-3' [SEQ ID NO: 10]

FW_R98S:
5'-cctttcacgtgatcagcatt-3' [SEQ ID NO: 11]

Rev_WTandR98S:
5'-gctctgataaaataatgcaagccta-3' [SEQ ID NO: 12].

---

The invention claimed is:

1. A method for increasing translation efficiency and fidelity of a target recombinant protein, the method comprising:
   (a) providing a mammalian host cell expressing a mutant RPL10 protein comprising a 98Ser amino acid substitution, wherein wild type RPL10 is not expressed or its expression is silenced within the mammalian cell, wherein the mammalian host cell is obtained from a cell line selected from the group consisting of Ba/F3, Jurkat, CHO, COS, Vero, Hela, BHK, HEK293, HEK293T, HKB-11, MEF, and Sp-2;
   (b) introducing to the mammalian host cell a nucleic acid encoding the target recombinant protein under conditions that allow expression of the target recombinant protein; and
   (c) recovering the expressed target recombinant protein from the mammalian host cell,
   wherein translation efficiency and fidelity of the target recombinant protein are increased compared to mammalian host cells expressing wild type RPL10.

2. The method according to claim 1, wherein an endogenous RPL10 DNA sequence has been deleted from the genome of the mammalian host cell, wherein expression of the endogenous RPL10 has been silenced, or wherein the endogenous RPL10 DNA sequence has been altered to encode the mutant RPL10 protein.

3. The method according to claim 1, wherein the mammalian host cells are grown in a medium comprising an antioxidant.

4. The method according to claim 1, wherein the mammalian host cells are grown in a medium comprising N-acetyl-L-cysteine (NAC).

5. The method according to claim 1, wherein NOTCH 1 signalling is activated in the mammalian host cells.

6. The method according to claim 5, wherein NOTCH 1 signalling is activated by transduction with a retroviral vector harbouring MSCV plasmids encoding activated intracellular NOTCH 1 (NOTCH 1-ICN).

7. A method for identifying an RPL10 mutation which results in increased expression of a recombinant protein in a cell comprising the RPL10 mutation compared to a cell comprising wild type RPL10, the method comprising:
   introducing in a first mammalian cell a first nucleic acid encoding a mutated RPL10 protein under conditions that allow expression of the mutated RPL10 protein, wherein wild type RPL10 is absent,
   introducing in the first mammalian cell a second nucleic acid encoding a detectable protein under conditions that allow expression of the detectable protein,
   introducing in a second mammalian cell a third nucleic acid encoding a wild type RPL10 protein under conditions that allow expression of the wild type RPL10 protein,
   introducing in the second mammalian cell the second nucleic acid encoding the detectable protein under conditions that allow expression of the detectable protein,
   cultivating the first mammalian cell and the second mammalian cell under the same conditions, and
   comparing the amount of detectable protein produced, wherein a mammalian cell with an RPL10 mutation wherein an increase of at least 2% (w/w) of detectable protein is obtained, is selected as host for the expression of recombinant proteins,
   wherein the first and second mammalian cells are obtained from a cell line selected from the group consisting of Ba/F3, Jurkat, CHO, COS, Vero, Hela, BHK, HEK293, HEK293T, HKB-11, MEF, and Sp-2.

8. The method according to claim 1, wherein the mammalian host cell is obtained from the Ba/F3 or Jurkat cell lines.

9. The method according to claim 1, wherein the mammalian host cell is obtained from the CHO cell line and the mammalian host cells are cultured in a medium comprising N-acetyl-L-cysteine (NAC).

10. The method according to claim 3, wherein the antioxidant is glutathione.

11. The method according to claim 1, wherein the mutant RPL10 is under control of an inducible promoter or is constitutively expressed in the mammalian host cell.

* * * * *